US011053144B2

(12) United States Patent
Fukuzawa et al.

(10) Patent No.: US 11,053,144 B2
(45) Date of Patent: Jul. 6, 2021

(54) BALLAST WATER MEASUREMENT DEVICE AND BALLAST WATER MEASUREMENT METHOD

(71) Applicant: KURITA WATER INDUSTRIES LTD., Tokyo (JP)

(72) Inventors: Kotaro Fukuzawa, Tokyo (JP); Kaname Harada, Tokyo (JP); Kazuhiko Tsunoda, Tokyo (JP); Minoru Yagi, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 0 days.

(21) Appl. No.: 16/485,075

(22) PCT Filed: Sep. 15, 2017

(86) PCT No.: PCT/JP2017/033513
§ 371 (c)(1),
(2) Date: Aug. 9, 2019

(87) PCT Pub. No.: WO2018/146849
PCT Pub. Date: Aug. 16, 2018

(65) Prior Publication Data

US 2019/0359509 A1 Nov. 28, 2019

(30) Foreign Application Priority Data

Feb. 10, 2017 (JP) ............................ JP2017-022925

(51) Int. Cl.
*C02F 1/76* (2006.01)
*C02F 1/68* (2006.01)
(Continued)

(52) U.S. Cl.
CPC ............... *C02F 1/685* (2013.01); *B63J 4/002* (2013.01); *C02F 1/008* (2013.01); *C02F 1/76* (2013.01);
(Continued)

(58) Field of Classification Search
None
See application file for complete search history.

(56) References Cited

U.S. PATENT DOCUMENTS 7,255,098 B1 * 8/2007 Boley ...................... F01N 9/00 123/679
2005/0165518 A1 * 7/2005 Reynolds ........... G05B 23/0264 701/21
2011/0114569 A1 * 5/2011 Kim ...................... C02F 1/4674 210/739

FOREIGN PATENT DOCUMENTS

JP S495094 A 1/1974
JP 2009139119 A 6/2009
(Continued)

OTHER PUBLICATIONS

Okamoto Yukihiko, "JFE Ballast Water Management System", JFE Giho., vol. 25, pp. 1-6, Feb. 2010.
(Continued)

*Primary Examiner* — Chester T Barry
(74) *Attorney, Agent, or Firm* — Moser Taboada

(57) ABSTRACT

An object of the present invention is to reduce the installation load, or the maintenance or the management load of a measurement device for ballast water that is measured for plural times, and to simplify the linkage between ballast water process equipment and a ballast water measurement device that are installed in a ship.
A measurement device (2, 52) includes, a first measuring part (6-1, 54-1) that measures water quality of a first ballast water, with referring to ballast water before processing as the
(Continued)

first ballast water and ballast water after the processing as a second ballast water, a second measuring part (6-2, 54-2) that measures water quality of the second ballast water, a reagent supply part (8) that is connected to the first measuring part and the second measuring part, and that supplies a reagent from one reagent container to the first measuring part and the second measuring part, a water discharge part (7) that is connected to the first measuring part and the second measuring part, and that discharges the first ballast water and the second ballast water each after the measurement, and a housing (4) that accommodates therein the first measuring part, the second measuring part, the reagent supply part, and the water discharge part.

6 Claims, 11 Drawing Sheets

(51) Int. Cl.
*B63J 4/00* (2006.01)
*C02F 1/00* (2006.01)
*C02F 1/78* (2006.01)
*G01N 21/78* (2006.01)
*G01N 31/22* (2006.01)
*G01N 33/18* (2006.01)
*C02F 103/00* (2006.01)

(52) U.S. Cl.
CPC ............... *C02F 1/78* (2013.01); *G01N 21/78* (2013.01); *G01N 31/22* (2013.01); *G01N 33/18* (2013.01); *C02F 2103/008* (2013.01)

(56) References Cited

FOREIGN PATENT DOCUMENTS

| | | | |
|---|---|---|---|
| JP | 2011528982 | A | 12/2011 |
| JP | 2012007969 | A | 1/2012 |
| WO | WO-2017017462 | A1 | 2/2017 |

OTHER PUBLICATIONS

International Search Report for application No. PCT/JP2017/033513 dated Dec. 5, 2017.

* cited by examiner

2(52)
14
CONTROL PART
6-2(54-2)
MEASURING PART
6-1(54-1)
MEASURING PART
110
CONTROL PART
102
BALLAST WATER PROCESS EQUIPMENT
104
WATER SUPPLY AND DISCHARGE LINE
126
[WATER DISCHARGE EXIT]
[BALLAST TANK]
130
122
128
124
134
138-2
120
FLOW METER
118
MIXER
136
138-3
[NEUTRALIZER]
108
[OXIDIZING AGENT]
106
138-1
132
116
B.P
114
112
[WATER INJECTION ENTRANCE]

BALLAST WATER MEASUREMENT DEVICE AND BALLAST WATER MEASUREMENT METHOD

TECHNICAL FIELD

The present invention relates to water quality measurement for ballast water loaded on a ship.

BACKGROUND ART

On a ship such as a cargo ship, the amount of the ballast water loaded on the ship is adjusted to suppress any draft variation of the ship caused by variation of the mount of the cargo. The ballast water is loaded at the anchorage site at which a cargo is disembarked and is discharged at the anchorage site at which another cargo is loaded. A ballast water process is known according to which an oxidizing agent such as sodium hypochlorite or ozone is injected into the ballast water such that any aquatic organisms and any pathogenic organisms included in the ballast water are annihilated, to prevent any oceanic pollution caused by the move of the aquatic organisms and the pathogenic organisms (such as, for example, Patent Document 1). In a ballast water discharge process, a ballast water process of neutralizing the ballast water by injecting thereinto a neutralizer is executed.

PRIOR ART DOCUMENT

Patent Document

Patent Document 1: Japanese Laid-Open Patent Publication No. 2012-007969

SUMMARY OF THE INVENTION

Problems to be Solved by the Invention

In the ballast water process executed at the time of the ballast water discharge process, for example, the water quality of the ballast water before the neutralization and the water quality of the ballast water after the neutralization are measured. Water quality information on the ballast water before the neutralization is used in the determination of the injection amount of the neutralizer, and water quality information on the ballast water after the neutralization is used in the water quality management of the ballast water to be discharged. In the ballast water process, for example, two water quality measurement sessions are executed. Assuming that one measurement device is installed for each of the sessions, it is necessary to secure the installation areas for the measurement devices and the work areas necessary for the operation or the maintenance of the measurement devices. On a ship where the installation areas for the devices are limited, a problem arises that the installation areas for the devices are insufficient. When the measurement devices for the water quality measurement are increased, another problem arises that the load of the maintenance and the management of the measurement devices is also increased and the linkage among the measurement devices becomes complicated.

An object of the present invention is to reduce the installation load, or the maintenance or the management load of the measurement devices for the ballast water that is measured for plural times.

Another object of the present invention is to simplify the linkage between ballast water process equipment and the ballast water measurement devices that are installed in a ship.

Means for Solving Problems

To achieve the above objective or objectives, according to an aspect of a ballast water measurement device of the present invention, with referring to ballast water before processing as a first ballast water and ballast water after the processing as a second ballast water, the ballast water measurement device includes a first measuring part that measures water quality of the first ballast water, a second measuring part that measures water quality of the second ballast water, a reagent supply part that is connected to the first measuring part and the second measuring part, and that supplies a reagent from one reagent container to the first measuring part and the second measuring part, a water discharge part that is connected to the first measuring part and the second measuring part, and that discharges the first ballast water and the second ballast water each after the measurement, and a housing that accommodates therein the first measuring part, the second measuring part, the reagent supply part, and the water discharge part.

The ballast water measurement device may include a buffer solution supply part that is connected to the first measuring part and the second measuring part, and that supplies a buffer solution from one buffer solution container to the first measuring part and the second measuring part.

The ballast water measurement device may include a cleaning liquid supply part that is connected to the first measuring part and the second measuring part, and that supplies a cleaning liquid from one cleaning liquid container to the first measuring part and the second measuring part.

The ballast water measurement device may be installed in a ship and may measure the water quality of the ballast water before and that after the ballast water process by ballast water process equipment installed in the ship.

In the ballast water measurement device, the reagent in the reagent container may be colored.

To achieve the above objective or objectives, according to an aspect of a ballast water measurement method of the present invention, with referring to ballast water before processing as a first ballast water and ballast water after the processing as a second ballast water, the ballast water measurement method includes supplying the first ballast water to a first measuring part in a housing, supplying the second ballast water to a second measuring part in the housing, supplying a reagent from one reagent container in the housing to the first measuring part and the second measuring part, measuring the first ballast water including the reagent using the first measuring part, measuring the second ballast water including the reagent using the second measuring part, and discharging the first ballast water and the second ballast water each after the measurement from one water discharge part in the housing.

Effect of the Invention

According to the present invention, any one of the following effects is achieved.

(1) The measurement device includes the first measuring part and the second measuring part, and the one measurement device can therefore measure the water quality of the ballast water at each of at least two points separately from each other. For example, on a ship on which the water quality of the ballast water before and that after processing are measured, the number of the measurement devices to be installed can be suppressed. The installation area for the measurement device for the ballast water, and the work area therefor can be reduced and the installation load of the measurement device can be reduced.

(2) The load on the shipmen maintaining and managing the measurement device can be reduced by suppressing the number of the installed measurement devices. For example, the reagent is supplied from the one reagent container to the first measuring part and the second measuring part, and the number of the reagent containers can therefore be reduced relative to the number of the types of ballast water to be measured. The load of the management of the remaining amount of the reagent in the reagent container is reduced by suppressing the number of the reagent containers.

(3) Linkage among the water quality measurement results is easy because the water quality of the ballast water at each of at least two points can be measured in the one housing.

Other objects, features, and advantages of the present invention will become more apparent when reading the embodiments herein with reference to the accompanying drawings.

MODES FOR CARRYING OUT THE INVENTION

First Embodiment

Figure 1:
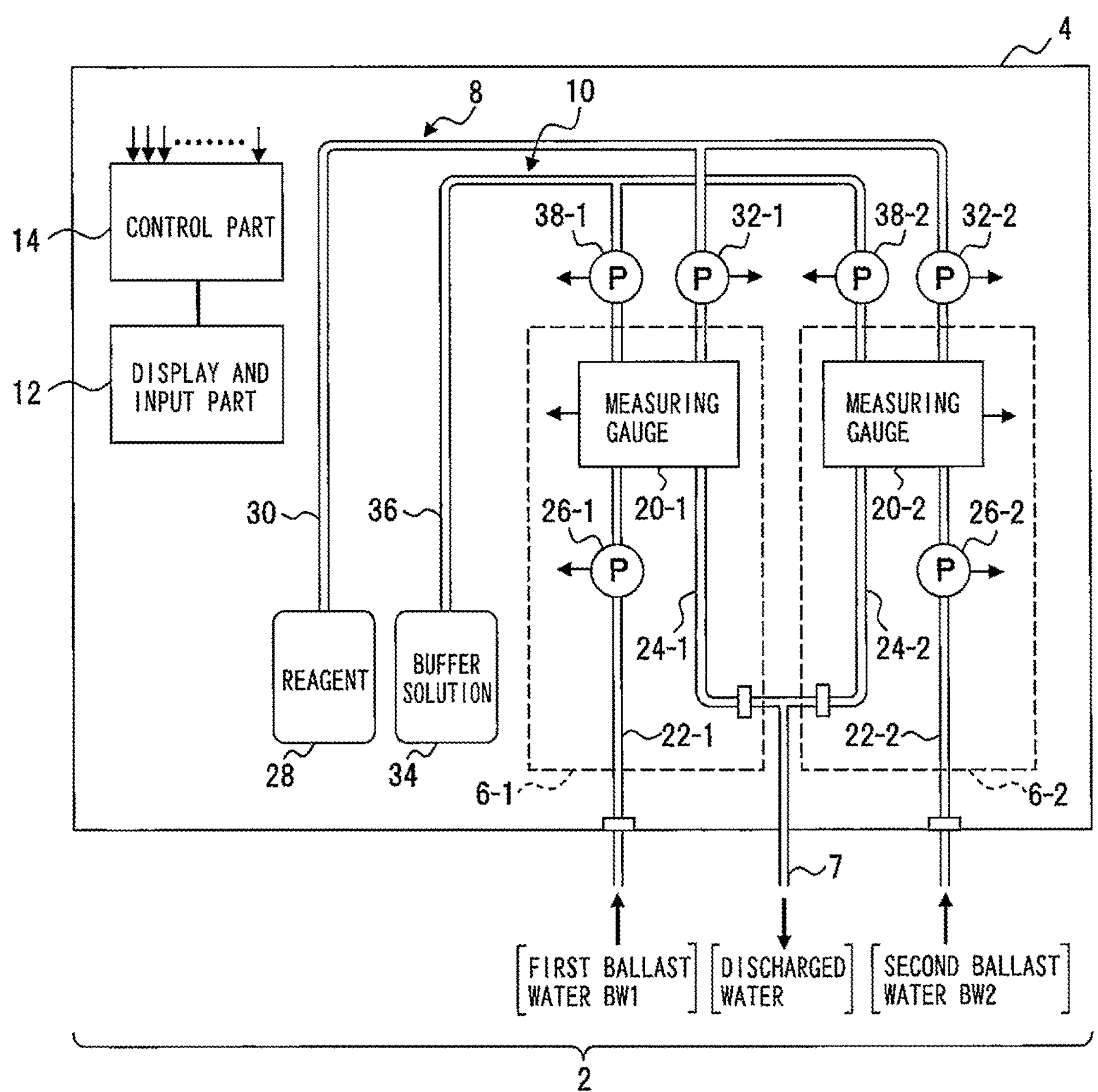
FIG. 1 is a diagram of an example of a ballast water measurement device according to a first embodiment.

A first embodiment will be described with reference to FIG. 1. FIG. 1 depicts an example of a ballast water measurement device according to the first embodiment. In FIG. 1, thin arrows attached to measuring gauges, pumps, and a control part indicate connections between the control part and the devices, and thick arrows attached to an entrance of a water supply pipe and an exit of a discharge part indicate flows of ballast water or discharge water.

A ballast water measurement device 2 (hereinafter, referred to as "measurement device 2") is an example of a measurement device that measures the water quality of plural types of ballast water such as, for example, the total residual oxidants (TRO) concentration of an oxidizing agent such as sodium hypochlorite or ozone included in the ballast water. The measurement device 2 includes a housing 4, a first measuring part 6-1 (hereinafter, referred to as "measuring part 6-1"), a second measuring part 6-2 (hereinafter, referred to as "measuring part 6-2"), a water discharge part 7, a reagent supply part 8, a buffer solution supply part 10, a display and input part 12, and a control part 14. To the measurement device 2, first ballast water BW1 (hereinafter, referred to as "ballast water BW1") and second ballast water BW2 (hereinafter, referred to as "ballast water BW2") are supplied. The ballast water BW1 is, for example, ballast water before undergoing a ballast water process of injecting thereinto an oxidizing agent or a neutralizer, and the ballast water BW2 is, for example, ballast water after undergoing the ballast water process.

The housing 4 accommodates therein the measuring parts 6-1 and 6-2, the water discharge part 7, the reagent supply part 8, the buffer solution supply part 10, the display and input part 12, and the control part 14, and aggregates these members in the housing. The housing 4 is, for example, a metal housing and imparts stiffness to the measurement device 2.

The measuring part 6-1 includes a first measuring gauge 20-1 (hereinafter, referred to as "measuring gauge 20-1"), a first water supply pipe 22-1 (hereinafter, referred to as "water supply pipe 22-1"), a first water discharge pipe 24-1 (hereinafter, referred to as "water discharge pipe 24-1"), and a first water supply pump 26-1 (hereinafter, referred to as "water supply pump 26-1"). The measuring gauge 20-1 is connected to the water supply pipe 22-1 and the water discharge pipe 24-1. The measuring gauge 20-1, the water supply pipe 22-1, and the water discharge pipe 24-1 form a first ballast water flow path. The water supply pump 26-1 is installed on the water supply pipe 22-1. The water supply pump 26-1 causes the ballast water BW1 in the first ballast water flow path to flow, by its operation.

The measuring gauge 20-1 is an example of the means for measuring the water quality of the ballast water BW1. The measuring gauge 20-1 measures, for example, the concentration of the TRO in the ballast water BW1. The measuring gauge 20-1 includes a colorimeter that measures the significance of absorption of light by the ballast water BW1. The colorimeter includes, for example, a light source and a measurement cell, and measures the significance of the absorption of the light by the ballast water BW1 that is caused to present a color corresponding to the TRO concentration by addition of a reagent. For example, when a diethyl-P-phenylenediamine (DPD) reagent is added to the ballast water BW1, this reagent reacts with the TRO to present a color of pink to pinkish red corresponding to the concentration of the TRO. This color is measured using a colorimeter using, for example, a DPD colorimetric method or a DPD absorptiometric method, and the water quality of the ballast water BW1 can thereby be measured.

The water supply pipe 22-1 supplies the ballast water BW1 to the measuring gauge 20-1 and the water discharge pipe 24-1 discharges the ballast water BW1 measured by the measuring gauge 20-1 to the water discharge part 7. The water supply pipe 22-1 and the water discharge pipe 24-1 only have to be pipes having corrosion resistance against the oxidizing agent included in the ballast water BW1 and only have to be, for example, resin pipes such as fluorine resin pipes or vinyl chloride pipes, stainless steel pipes, or metal pipes to which a corrosion prevention process is applied.

The measuring part 6-2 includes a second measuring gauge 20-2 (hereinafter, referred to as "measuring gauge 20-2"), a second water supply pipe 22-2 (hereinafter, referred to as "water supply pipe 22-2"), a second water discharge pipe 24-2 (hereinafter, referred to as "water discharge pipe 24-2"), and a second water supply pump 26-2 (hereinafter, referred to as "water supply pump 26-2"). The measuring gauge 20-2 is connected to the water supply pipe 22-2 and the water discharge pipe 24-2. The measuring gauge 20-2, the water supply pipe 22-2, and the water discharge pipe 24-2 form a second ballast water flow path. The water supply pump 26-2 is installed on the water supply pipe 22-2. The water supply pump 26-2 causes the ballast water BW2 in the second ballast water flow path to flow, by its operation.

The measuring gauge 20-2 is an example of the means for measuring the water quality of the ballast water BW2. The measuring gauge 20-2 measures, for example, the TRO concentration of the ballast water BW2. The measuring gauge 20-2 includes, for example, the above colorimeter and measures the water quality in the ballast water BW2 by adding the reagent.

The water supply pipe 22-2 supplies the ballast water BW2 to the measuring gauge 20-2 and the water discharge pipe 24-2 discharges the ballast water BW2 measured by the measuring gauge 20-2 to the water discharge part 7. The water supply pipe 22-2 and the water discharge pipe 24-2 only have to be pipes having corrosion resistance against the oxidizing agent included in the ballast water BW2 and only have to be, for example, resin pipes such as fluorine resin pipes or vinyl chloride pipes, stainless steel pipes, or metal pipes to which a corrosion prevention process is applied.

The water discharge part 7 is an example of the means for conveying the discharged water, includes branch pipes that extend on the outer side of the housing 4 and in two directions in the housing, and forms an exit pipe for the two types of ballast water BW1 and BW2. One of the pipes extending in the two directions in the housing is connected to the water discharge pipe 24-1 of the measuring part 6-1, and the other one of the pipes extending in the two directions in the housing is connected to the water discharge pipe 24-2 of the measuring part 6-2. The water discharge part 7 causes the ballast water BW1 and the ballast water BW2 to join each other and collectively discharges these to the exterior of the housing 4. The water discharge part 7 only has to be a pipe having corrosion resistance against the oxidizing agent included in the types of ballast water BW1 and BW2, and only has to be, for example, a resin pipe such as a fluorine resin pipe or a vinyl chloride pipe, a stainless steel pipe, or a metal pipe to which a corrosion prevention process is applied.

The measuring part 6-1 and the measuring part 6-2 are arranged, for example, to be symmetric in the right-and-left direction about an extended line passing through the water discharge part 7. The arrangement of each of the measuring part 6-1 and the measuring part 6-2 does not need to be learned separately from each other and the load of handling the measurement device 2 is reduced by arranging the measuring part 6-1 and the measuring part 6-2 to be symmetric in the right-and-left direction.

The reagent supply part 8 includes a reagent container 28, a reagent pipe 30, a first reagent supply pump 32-1 (hereinafter, referred to as "reagent supply pump 32-1"), and a second reagent supply pump 32-2 (hereinafter, referred to as "reagent supply pump 32-2"). The reagent container 28 is an example of a reagent storing part that stores therein the reagent. The reagent container 28 is connected through the reagent pipe 30 to, for example, the measuring gauge 20-1 of the measuring part 6-1, and the measuring gauge 20-2 of the measuring part 6-2. The reagent pipe 30 is an example of the means for conveying the reagent and, for the reagent pipe 30, a pipe connected to the reagent container 28 is branched to form two branch pipes. One of the branch pipes is connected to the measuring gauge 20-1 and the other branch pipe is connected to the measuring gauge 20-2. The reagent pipe 30 only has to be a pipe having chemical resistance against the reagent, and only has to be, for example, a resin pipe such as a fluorine resin pipe or a vinyl chloride pipe, a stainless steel pipe, or a metal pipe to which a corrosion prevention process is applied.

The reagent supply pump 32-1 is installed on the branch pipe connected to the measuring gauge 20-1. The reagent supply pump 32-1 supplies the reagent in the reagent container 28 to the measuring gauge 20-1, by being driven. The reagent supply pump 32-2 is installed on the branch pipe connected to the measuring gauge 20-2. The reagent supply pump 32-2 supplies the reagent in the reagent container 28 to the measuring gauge 20-2, by being driven.

The reagent only has to react with the TRO to present a color and, for example, the DPD reagent is usable.

The buffer solution supply part 10 includes a buffer solution container 34, a buffer solution pipe 36, a first buffer solution supply pump 38-1 (hereinafter, referred to as "buffer solution supply pump 38-1"), and a second buffer solution supply pump 38-2 (hereinafter, referred to as "buffer solution supply pump 38-2"). The buffer solution container 34 is an example of a buffer solution storing part that stores therein the buffer solution. The buffer solution container 34 is connected through the buffer solution pipe 36 to, for example, the measuring gauge 20-1 of the measuring part 6-1 and the measuring gauge 20-2 of the measuring part 6-2. The buffer solution pipe 36 is an example of the means for conveying the buffer solution and, for the buffer solution pipe 36, the pipe connected to the buffer solution container 34 is branched to form two branch pipes. One of the branch pipes is connected to the measuring gauge 20-1 and the other branch pipe is connected to the measuring gauge 20-2. The buffer solution pipe 36 only has to be a pipe having chemical resistance against the buffer solution, and only has to be, for example, a resin pipe such as a fluorine resin pipe or a vinyl chloride pipe, a stainless steel pipe, or a metal pipe to which a corrosion prevention process is applied.

The buffer solution supply pump 38-1 is installed on the branch pipe connected to the measuring gauge 20-1. The buffer solution supply pump 38-1 supplies the buffer solution in the buffer solution container 34 to the measuring gauge 20-1, by being driven. The buffer solution supply pump 38-2 is installed on the branch pipe connected to the measuring gauge 20-2. The buffer solution supply pump 38-2 supplies the buffer solution in the buffer solution container 34 to the measuring gauge 20-2, by being driven.

The buffer solution only has to be a solution to adjust the hydrogen-ion concentration of the types of ballast water BW1 and BW2 measured by the measuring gauges 20-1 and 20-2 and is, for example, a phosphate buffer solution.

The display and input part 12 displays thereon information based on an output of the control part 14, and receives an operation to produce instruction information for the measurement device 2. The display and input part 12 includes a display such as, for example, a liquid crystal display, a light emitting diode (LED) display, or an organic EL display. Receiving an output of the control part 14, the display and input part 12 displays thereon pieces of measurement device information such as, for example, pieces of water quality information on the types of ballast water BW1 and BW2, operation information on the measurement device 2, and alarm information. The display and input part 12 further includes, for example, a touch panel and produces instruction information such as setting information for the measurement device 2 and switching information for the display, based on an operation.

Figure 2:
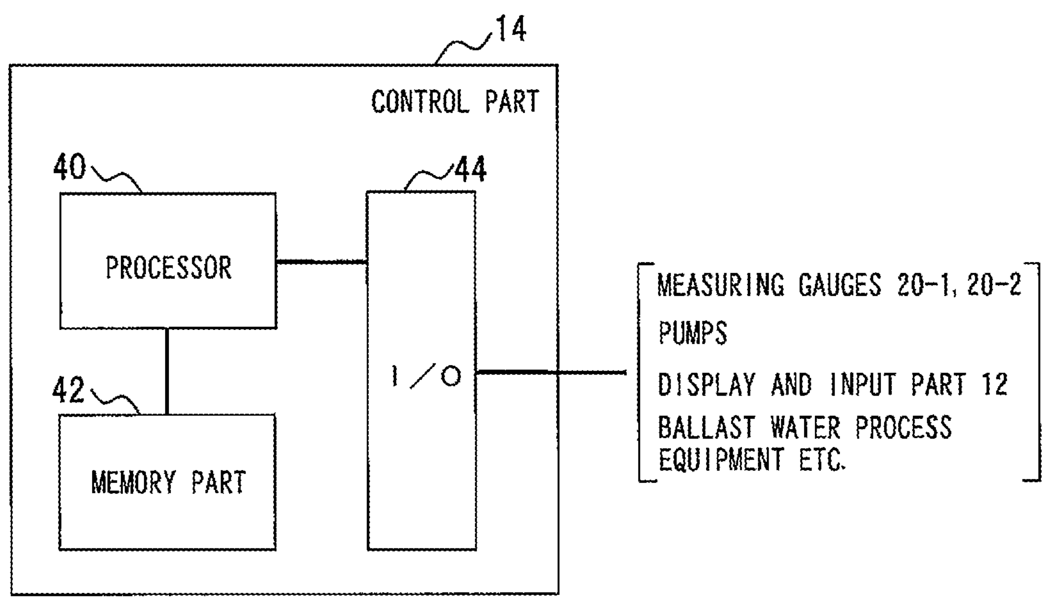
FIG. 2 is a diagram of an example of the hardware configuration of a control part.

The control part 14 is an example of a computer that includes a water quality measurement function, an output function for measurement results, and a communication function for external instruments. FIG. 2 depicts an example of the hardware configuration of the control part 14. The control part 14 includes a processor 40, a memory part 42, and an input-output (I/O) 44.

The processor 40 is an example of an information processing part that processes information and is, for example, a central processing unit (CPU). The processor 40 executes an operating system (OS) and a water quality measurement program that are stored in the memory part 42, and executes various types of information processing. The information processing executed by the processor 40 includes an instruction for operation or stoppage of each of the pumps, an instruction for operation or stoppage of the measuring gauges 20-1 and 20-2, processing of the measurement values acquired by the measuring gauges 20-1 and 20-2, outputting of the measurement device information, processing of the instruction information produced by the display and input part 12, and control for inputting and outputting by the I/O 44.

The memory part 42 stores therein the programs such as the OS and the water quality measurement program executed by the processor 40. In the memory part 42, storing or reading of the various types of information is executed in accordance with the control by the processor 40. The memory part 42 includes one or plural ones of storing elements such as a read-only memory (ROM), a random-access memory (RAM), an electrically erasable programmable read-only memory (EEPROM), a NAND-type flash memory, and a NOR-type flash memory. A hard disc device or a semiconductor storage device may be used as one of the storing elements.

The I/O 44 is connected by wire or by radio to connection instruments such as the measuring gauges 20-1 and 20-2, the pumps, the display and input part 12, and the ballast water process equipment. The I/O 44 is used for transmission and reception of data between the processor 40 and the connection instruments.

[Water Quality Measurement for Types of Ballast Water BW1 and BW2]

Figure 3:
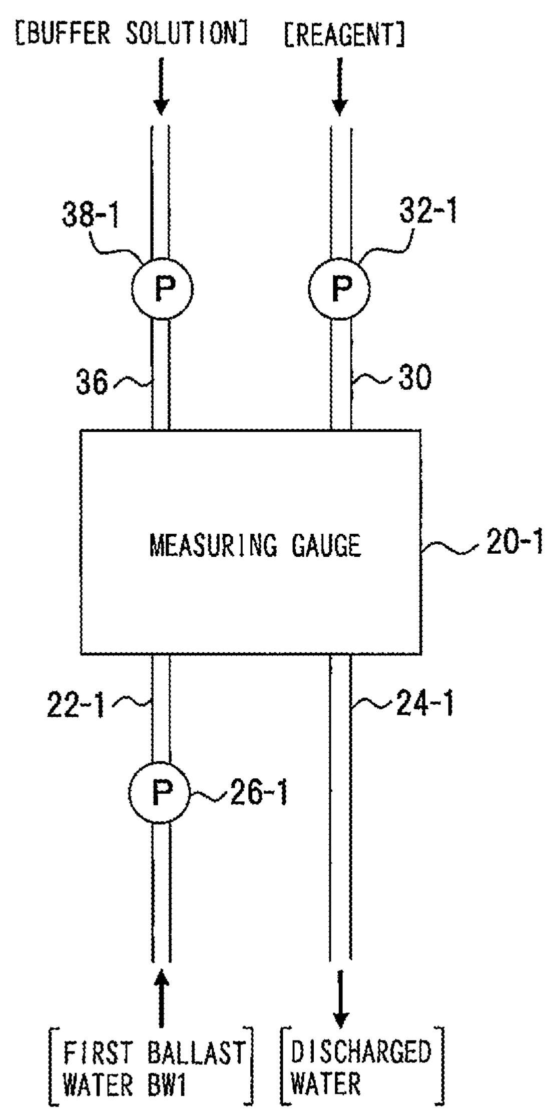
FIG. 3 is a diagram of a measuring gauge and pipes connected to the measuring gauge.

The water quality measurement for the types of ballast water BW1 and BW2 will be described with reference to FIG. 3. FIG. 3 depicts the measuring gauge 20-1 and the pipes connected to the measuring gauge 20-1. Arrows in FIG. 3 each indicate the flow of the ballast water, the discharged water, the reagent, or the buffer solution.

The first ballast water BW1 is supplied to the measuring gauge 20-1 through the water supply pipe 22-1 and the water supply pump 26-1. The reagent is supplied to the measuring gauge 20-1 through the reagent pipe 30 and the reagent supply pump 32-1. The buffer solution is supplied to the measuring gauge 20-1 through the buffer solution pipe 36 and the buffer solution supply pump 38-1. The first ballast water BW1, the reagent, and the buffer solution supplied to the measuring gauge 20-1 are mixed with each other in the measuring gauge 20-1 by, for example, a stirring device where a stirring bar and a stirrer are included. The mixing of these causes the reagent to react with the TRO in the first ballast water BW1 to present a color of pink to pinkish red. The buffer solution adjusts the hydrogen-ion concentration of the ballast water BW1.

The measuring gauge 20-1 measures the concentration of the TRO of the ballast water BW1 that includes the DPD reagent and the buffer solution using, for example, the DPD colorimetric method or the DPD absorptiometric method. The TRO concentration of the ballast water BW1 only has to be measured based on, for example, the DPD colorimetric method described in Section 33.2 of Japanese Industrial Standard JIS K0102(2013) or the DPD absorptiometric method described in Section 33.4 therein, or the DPD colorimetric method 4500-C1 G approved by the United States Environmental Protection Agency.

The ballast water BW1 after undergoing the water quality measurement is discharged through the water discharge pipe 24-1 as the discharged water. The water quality of the ballast water BW2 only has to be measured in the same manner as that for the water quality of the ballast water BW1 using the measuring gauge 20-2, the water supply pipe 22-2, the water supply pump 26-2, the reagent pipe 30, the reagent supply pump 32-2, the buffer solution pipe 36, the buffer solution supply pump 38-2, and the water discharge pipe 24-2. The water quality measurement for the ballast water BW2 will not again be described.

[Display of Result of Water Quality Measurement]

Figure 4:
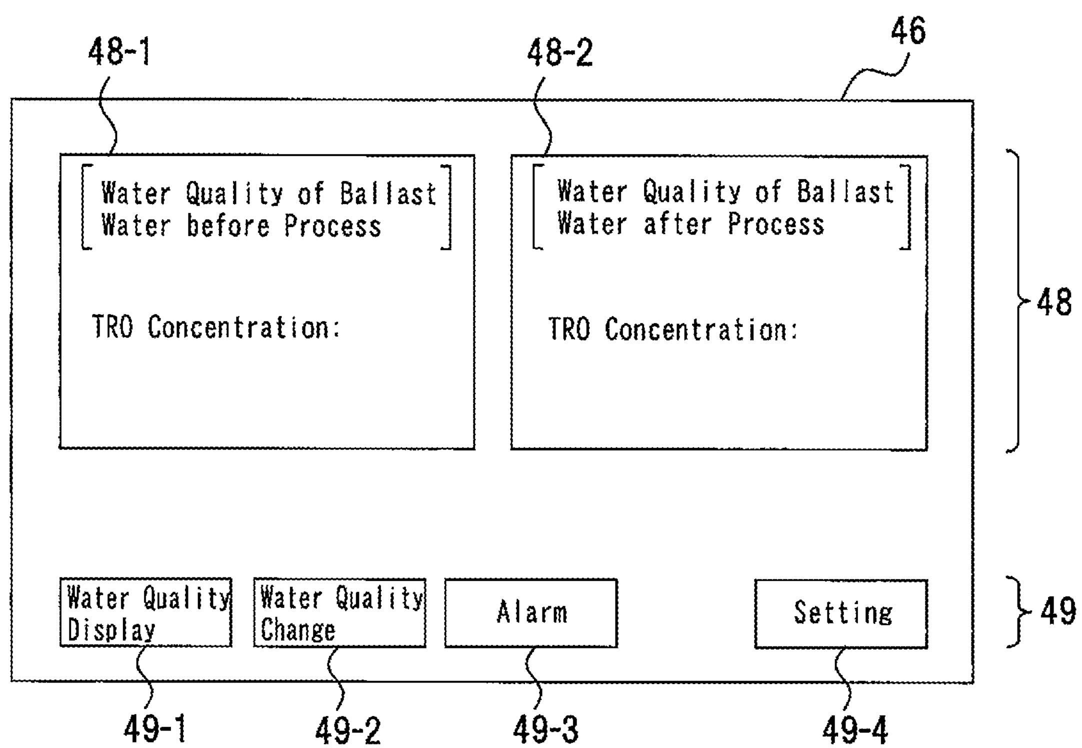
FIG. 4 is a diagram of an example of display of a result of water quality measurement.

The display of the result of the water quality measurement for the types of ballast water BW1 and BW2 will be described with reference to FIG. 4. FIG. 4 depicts an example of the display of the result of the water quality measurement. A display screen 46 is displayed by the display and input part 12 based on a display instruction output by the control part 14.

The display screen 46 includes a display area 48 and an operational area 49. In the display area 48, information on a selection item selected by an operation in the operational area 49 is displayed. For example, when a selection item "Water Quality Display" is selected, the display area 48 is displayed that includes, for example, a first display area 48-1 and a second display area 48-2. In the first display area 48-1, the water quality information on the ballast water BW1 such as, for example, the water quality of the ballast water before undergoing the ballast water process is displayed. In the second display area 48-2, the water quality information on the ballast water BW2 such as, for example, the water quality of the ballast water after undergoing the ballast water process is displayed. In the first display area 48-1, the water quality of the ballast water such as, for example, the TRO concentration is displayed together with, for example, the display item "Water Quality of Ballast Water before Process". In the second display area 48-2, the water quality of the ballast water such as, for example, the TRO concentration is displayed together with, for example, the display item "Water Quality of Ballast Water after Process".

In the operational area 49, operational buttons for the selection items to be displayed in the display area 48 are displayed. The operational buttons include, for example, a selection button 49-1 to display a selection item "Water Quality Display", a selection button 49-2 to display a selection item "Water Quality Change", a selection button 49-3 to display a selection item "Alarm", and a selection button 49-4 to display a selection item "Setting". The example where the water quality information is displayed in the display area 48 is depicted in FIG. 4 while the changes of the water quality of the types of ballast water BW1 and BW2 only have to be displayed in the display area 48 when the selection item "Water Quality Change" is selected, alarm information such as, for example, a currently issued alarm and an alarm history only has to be displayed in the display area 48 when the selection item "Alarm" is selected, and setting items for the measurement device 2 only have to be displayed in the display area 48 when the selection item "Setting" is selected.

[Process Procedure for Water Quality Measurement for Types of Ballast Water BW1 and BW2]

Figure 5:
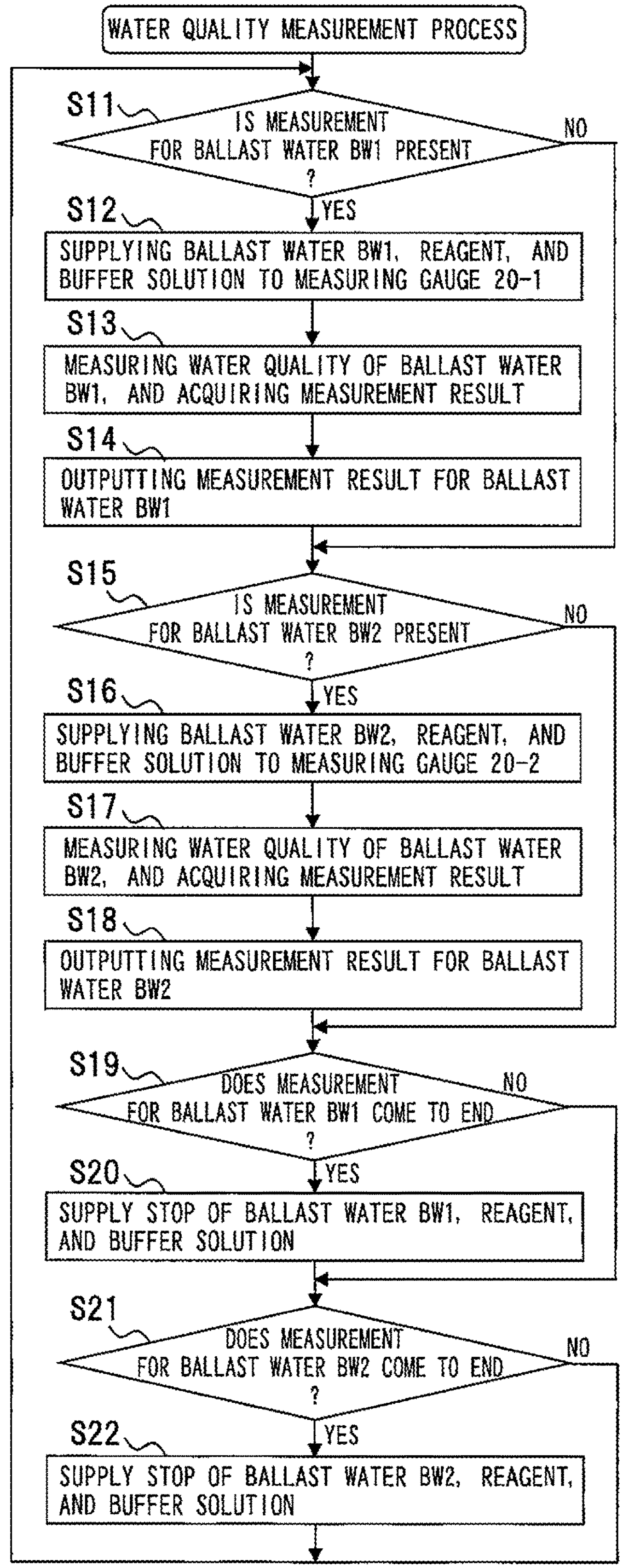
FIG. 5 is a flowchart of an example of a process procedure for the water quality measurement.

The process procedure for the water quality measurement for the types of ballast water BW1 and BW2 will be described with reference to FIG. 5. FIG. 5 is a flowchart of an example of the process procedure for the water quality measurement. The process procedure for the water quality measurement is an example of the ballast water measurement method of the present invention, and is processed by the control part 14. In FIG. 5, "step S" represents a stage of the process.

The control part 14 determines whether measurement for the ballast water BW1 is present (step S11). When the control part 14 determines that the measurement for the ballast water BW1 is present (YES of step S11), the control part 14 executes a first water quality measurement process (steps S12 to S14). In the first water quality measurement process, the control part 14 operates the water supply pump 26-1, the reagent supply pump 32-1, and the buffer solution supply pump 38-1 to supply the ballast water BW1, the reagent, and the buffer solution to the measuring gauge 20-1 (step S12), thereafter causes the measuring gauge 20-1 to measure the water quality of the ballast water BW1, and acquires the measurement result for the ballast water BW1 from the measuring gauge 20-1 (step S13). The ballast water BW1 after the measurement is discharged from the water discharge part 7. The control part 14 outputs the acquired measurement result to, for example, the display and input part 12 and the ballast water process equipment (step S14). When the control part 14 determines that the measurement for the ballast water BW1 is not present (NO of step S11), the control part 14 does not execute the first water quality measurement process (steps S12 to S14). Whether the measurement for the ballast water BW1 is present only has to be determined by, for example, acquiring the ballast water process information from the ballast water process equipment. The ballast water process information only has to include, for example, the information that indicates whether the ballast water process is currently executed.

The control part 14 determines whether measurement for the ballast water BW2 is present (step S15). When the control part 14 determines that the measurement for the ballast water BW2 is present (YES of step S15), the control part 14 executes a second water quality measurement process (steps S16 to S18). In the second water quality measurement process, the control part 14 operates the water supply pump 26-2, the reagent supply pump 32-2, and the buffer solution supply pump 38-2 to supply the ballast water BW2, the reagent, and the buffer solution to the measuring gauge 20-2 (step S16), thereafter causes the measuring gauge 20-2 to measure the water quality of the ballast water BW2, and acquires the measurement result for the ballast water BW2 from the measuring gauge 20-2 (step S17). The ballast water BW2 after the measurement is discharged from the water discharge part 7. The control part 14 outputs the acquired measurement result to, for example, the display and input part 12 and the ballast water process equipment (step S18). When the control part 14 determines that the measurement for the ballast water BW2 is not present (NO of step S15), the control part 14 does not execute the second water quality measurement process (steps S16 to S18). Whether the measurement for the ballast water BW2 is present only has to be determined by, for example, acquiring the ballast water process information from the ballast water process equipment.

The control part 14 determines whether the measurement for the ballast water BW1 comes to an end (step S19). When the control part 14 determines that the measurement for the ballast water BW1 comes to an end (YES of step S19), the control part 14 stops the water supply pump 26-1, the reagent supply pump 32-1, and the buffer solution supply pump 38-1 to stop the supply of the ballast water BW1, the reagent, and the buffer solution (step S20). When the control part 14 determines that the measurement for the ballast water BW1 does not come to an end (NO of step S19), that is, the measurement for the ballast water BW1 is present or is currently discontinued, the control part 14 does not execute step S20. Whether the measurement for the ballast water BW1 comes to an end only has to be determined by, for example, acquiring the ballast water process information from the ballast water process equipment.

The control part 14 determines whether the measurement for the ballast water BW2 comes to an end (step S21). When the control part 14 determines that the measurement for the ballast water BW2 comes to an end (YES of step S21), the control part 14 stops the water supply pump 26-2, the reagent supply pump 32-2, and the buffer solution supply pump 38-2 to stop the supply of the ballast water BW2, the reagent, and the buffer solution (step S22). When the control part 14 determines that the measurement for the ballast water BW2 does not come to an end (NO of step S21), that is, the measurement for the ballast water BW2 is present or is currently discontinued, the control part 14 does not execute step S22. Whether the measurement for the ballast water BW2 comes to an end only has to be determined by, for example, acquiring the ballast water process information from the ballast water process equipment.

The control part 14 repeats this process procedure to be able to continuously or intermittently measure the water quality of each of the types of ballast water BW1 and BW2. The first water quality measurement process and the second water quality measurement process are each processed separately from each other, and the control part 14 therefore not only can process both of the first water quality measurement process and the second water quality measurement process but also can process either the first water quality measurement process or the second water quality measurement process.

Effects of First Embodiment (1) The water quality of the types of ballast water at the two points can be measured separately from each other using the one measurement device 2. During the ballast water process by the neutralizer executed when the ballast water is discharged to the exterior of the ship, the one measurement device can measure the water quality of, for example, the ballast water before and that after the injection of the neutralizer. The number of installed water quality measurement devices for the ballast water can be suppressed that are installed together with the ballast water process equipment on the ship. The measurement device 2 is also usable in the water quality measurement for the ballast water executed when the ballast water is taken into the ship.

When the ballast water process equipment acquires the water quality information on the ballast water before the injection of the neutralizer, the ballast water process equipment can adjust the injection amount of the neutralizer in accordance with this water quality information. When the ballast water process equipment acquires the water quality information on the ballast water after the injection of the neutralizer, the water quality information on the ballast water before being discharged can be learned or recorded.

(2) The water discharge part 7, the reagent supply part 8, the buffer solution supply part 10, the display and input part 12, and the control part 14 are used in common by the two measuring parts 6-1 and 6-2, and the areas necessary for installing these members are therefore reduced. The installation area of the measurement device 2 can therefore be reduced and the work area necessary for the operation or the maintenance of the measurement device 2 can be reduced.

(3) The water quality of each of the types of ballast water at the two points is measured by the one measurement device, and the linkage load can be reduced between the ballast water process equipment and the measurement device 2. When the water quality of the ballast water at each of the two points is measured in the water intake process or the water discharge process for the ballast water, the ballast water process equipment does not need to be linked with any plural measurement devices and the linkage is therefore easy.

(4) The number of the measurement device 2, the number of the reagent container 28, and the number of the buffer solution container 34 are each smaller than the number of the water quality measurement points for the ballast water, and the load of equipment management for the measurement device 2 and the load of remaining amount management for the reagent and the buffer solution can be reduced.

(5) The pieces of water quality of the types of ballast water at the two points can be displayed being placed side by side on the display and input part 12 of the one measurement device 2. The manager of the ballast water process equipment can place the water quality before and that after the ballast water process using a drug such as, for example, the oxidizing agent or the neutralizer side by side in one screen to compare therebetween, and can efficiently learn the water quality of the ballast water.

Modification Examples (1) The water supply pump 26-1 is installed on the water supply pipe 22-1 and the water supply pump 26-2 is installed on the water supply pipe 22-2 in the above embodiment while the state of each of the types of ballast water BW1 and BW2 in the measuring parts 6-1 and 6-2 only has to be switched into a flowing water state or a static water state, and the embodiment is not limited to the installation of the water supply pumps 26-1 and 26-2. For example, open-close valves may be installed instead of the water supply pumps 26-1 and 26-2, and the state of each of the types of ballast water BW1 and BW2 may be switched into the flowing water state or the static water state by opening or closing each of the open-close valves. When the open-close valves are opened, the types of ballast water BW1 and BW2 flow into the measuring gauges 20-1 and 20-2 by the water pressures of the types of ballast water BW1 and BW2 and, when the open-close valves are closed, the types of ballast water BW1 and BW2 can be stopped each as static water.

The water supply pumps 26-1 and 26-2, or the above open-close valves may be respectively installed on the water discharge pipes 24-1 and 24-2. The state of each of the types of ballast water BW1 and BW2 may be switched into the flowing water state or the static water state by installing the water supply pumps or the open-close valves upstream the measurement device 2. When the water supply pumps or the open-close valves are installed upstream the measurement device 2, the water supply pumps 26-1 and 26-2 and the open-close valves of the measuring parts 6-1 and 6-2 can be excluded and the measurement device 2 can be simplified.

Figure 6:
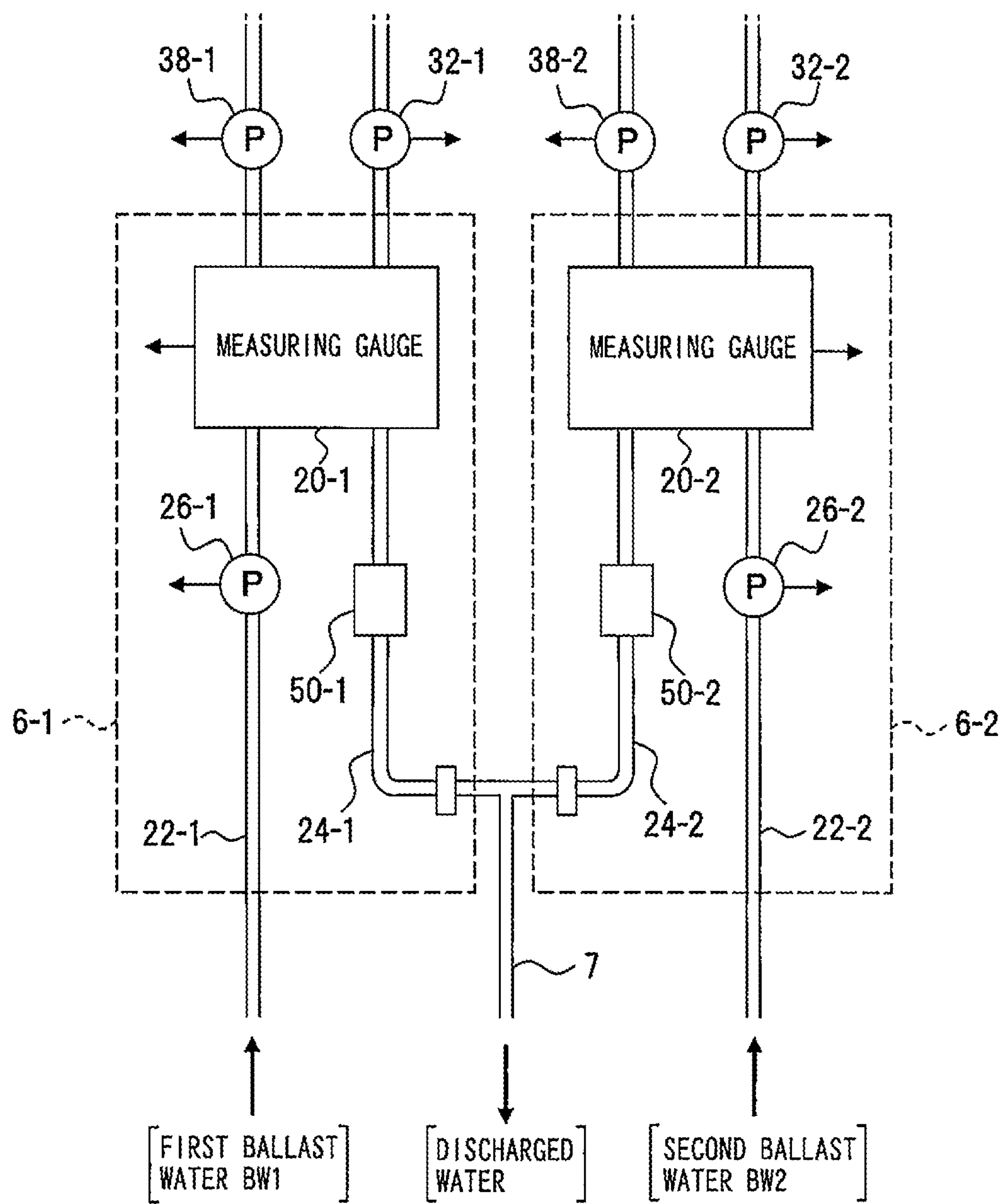
FIG. 6 is a diagram of an example of a ballast water measurement device according to a modification example.

(2) As depicted in FIG. 6, the water discharge pipes 24-1 and 24-2 may be provided with backflow preventing parts 50-1 and 50-2 preventing any backflow of the discharged water. The backflow preventing parts 50-1 and 50-2 only have to be, for example, backflow preventing valves or open-close valves that are each opened or closed by a control signal of the control part. The backflow preventing part 50-1 to be installed on the water discharge pipe 24-1 prevents the discharged water in the measuring part 6-2 from flowing into the measuring part 6-1, and the backflow preventing part 50-2 to be installed on the water discharge pipe 24-2 prevents the discharged water in the measuring part 6-1 from flowing into the measuring part 6-2. When either the measuring part 6-1 or the measuring part 6-2 operates, any application of the pressure of the discharged water to the measuring part 6-1 or the measuring part 6-2 that is does not operate can be suppressed and any pollution of the measuring part 6-1 or the measuring part 6-2 by the discharged water can be suppressed.

(3) The display and input part 12 having the display function and the input function is included in the above embodiment while a displaying part and an input part may be included therein separately from each other. The measurement device information may be displayed on an external displaying device connected to the measurement device 2. Instruction information produced by an external input device connected to the measurement device 2 may be received.

(4) The TRO concentration of each of the types of ballast water BW1 and BW2 is measured by supplying the DPD agent while the measurement is not limited to the one using the DPD reagent. For example, the TRO concentration may be measured using potassium iodide as the reagent to use iodine produced by the reaction between this potassium iodide and the TRO, and other water quality elements each including the TRO may be measured.

(5) The reagent used in the water quality measurement for the types of ballast water BW1 and BW2 may be colored to be, for example, blue in its initial state. When the colored reagent is used, the types of ballast water BW1 and BW2 including the reagent each have the color presented by the reaction between the reagent and the TRO, and the color retained from the initial state. When the color presented by the reagent and the color in the initial state are measured by each of the measuring gauges 20-1 and 20-2, the control part 14 can detect the TRO concentrations and the empty states without the reagent. In the case where the empty state occurs, when the control part 14 outputs the empty state information to the ballast water process equipment, the ballast water process equipment can temporarily discontinue the ballast water process. This outputting of the empty state information to the ballast water process equipment can prevent any malfunction caused by lack of the reagent such as, for example, suppression of injection of the neutralizer based on wrong determination as excessive injection of the neutralizer. Any discharging of insufficiently neutralized ballast water is prevented.

When the control part 14 notifies of the empty state of the reagent, a trigger for replenishing the reagent can be provided. The shipmen only have to replenish the reagent based on the notification for the empty state, and any monitoring of the remaining amount of the reagent such that the reagent does not run out is unnecessary. The load on the shipmen is reduced. When the empty state information on the reagent is adapted to be notified of to a management center on the land through, for example, a satellite line, the management center can recognize the lack of the reagent. This notification of the empty state information is automatically executed by the control part 14 of the measurement device 2, and no shipman therefore intervenes therebetween and any unexecuted notification can be prevented. The management center having the empty state information received therein can instruct a proper measure to the ship and can improve reduction of the time period to cope with any defect and processing quality of the ballast water process.

(6) The measurement device 2 includes the two measuring parts 6-1 and 6-2 in the above embodiment while the measurement device 2 may include three or more measuring parts. Even when the number of the measuring parts is three or more, the supply of the reagent and the buffer solution is not degraded and can be controlled by the control part 14.

(7) The water quality information on the ballast water BW1 and the water quality information on the ballast water BW2 are displayed being placed side by side in the display screen 46 in the embodiment while the display method is not limited to the above display method. For example, when the water quality information on the ballast water BW1 and the water quality information on the ballast water BW2 are each displayed in a screen different from that of each other, many pieces of water quality information on each of the types of ballast water BW1 and BW2 can be displayed. When the water quality display, the water quality change, and the information on alarms are displayed in one display screen, the load of switching the display can be alleviated.

(8) The device specification of each of the measuring parts 6-1 and 6-2 such as, for example, the measurement range and the sensitivity for the TRO concentration may be equal to each other or may be different from each other. When the device specifications of the measuring parts 6-1 and 6-2 are different from each other, the ballast water before and that after the process can be measured using the measuring part 6-1 or 6-2 that is more suitable for the measurement, and the measurement function of the measurement device 2 can be enhanced. For example, it is preferred that the ballast water before the neutralization process that includes a large amount of oxidizing agent be measured for a wide range by the measuring part having a wider measurement range, and it is preferred that the ballast water after the neutralization process that includes a small amount of oxidizing agent or no oxidizing agent be highly precisely measured by the measuring part having a higher sensitivity.

(9) The measuring part 6-1 measures the water quality of the ballast water BW1 before the ballast water process and the measuring part 6-2 measures the water quality of the ballast water BW2 after the ballast water process in the above embodiment while the measuring part 6-1 only has to measure the water quality of the ballast water BW1 and the measuring part 6-2 only has to measure the water quality of the ballast water BW2, and the water quality measurement is not limited to the above water quality measurement. For example, the measuring part 6-1 may further measure the water quality of the ballast water BW2 and the measuring part 6-2 may further measure the water quality of the ballast water BW1.

Second Embodiment

Figure 7:
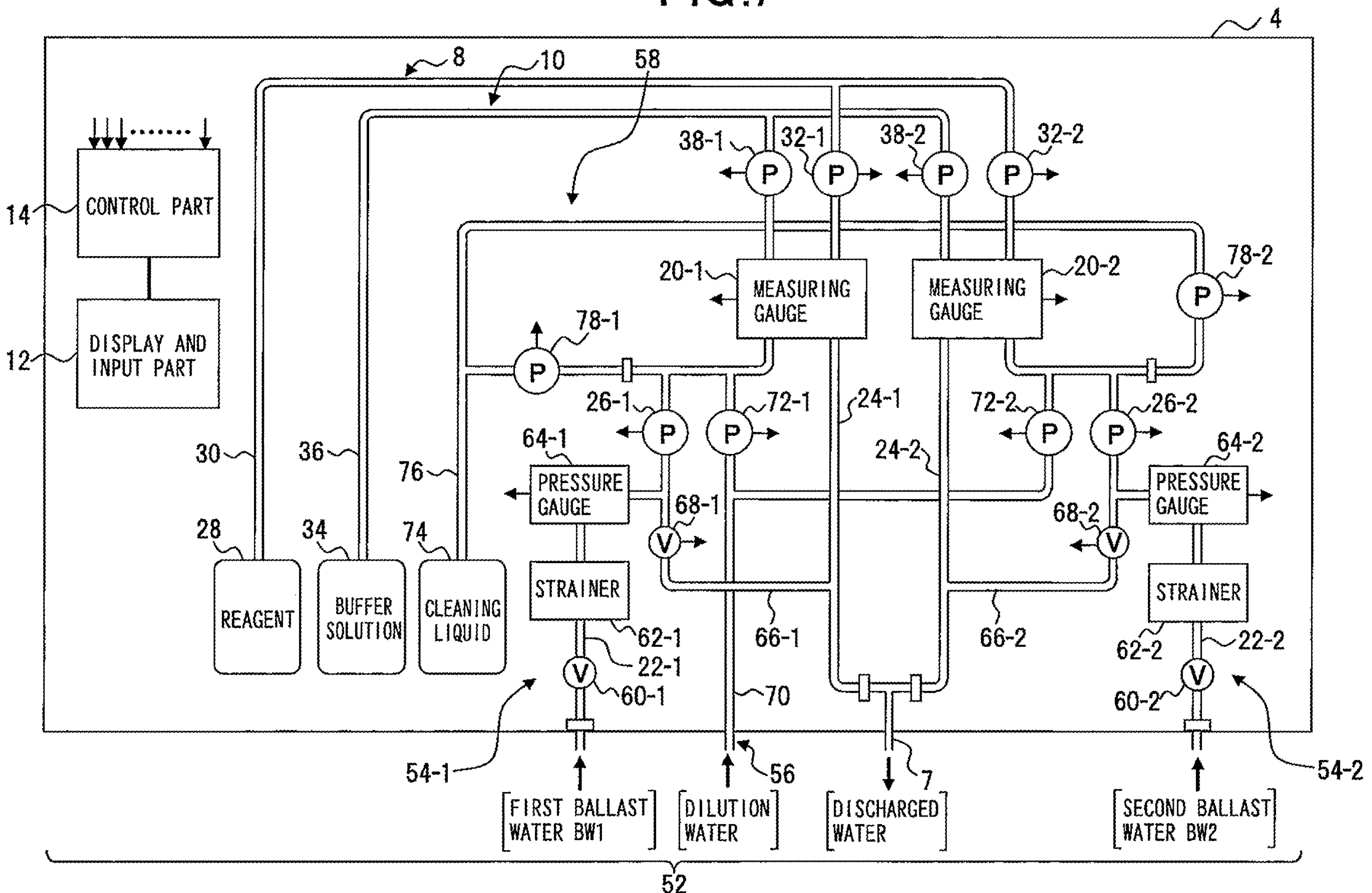
FIG. 7 is a diagram of an example of a ballast water measurement device according to a second embodiment.

A second embodiment will be described with reference to FIG. 7. FIG. 7 depicts an example of a ballast water measurement device according to the second embodiment.

In FIG. 7, parts same as those in FIG. 1 are given the same reference numerals. In FIG. 7, thin arrows attached to the devices such as measuring gauges and the pumps, and the control part indicate the connection between the control part and the devices, and thick arrows attached to entrances of the water supply pipes, an exit of the water discharge part, and an entrance of a dilution water pipe indicate the directions of the flows of the ballast water, the discharged water, or dilution water.

A ballast water measurement device 52 (hereinafter, referred to as "measurement device 52") is an example of the measurement device that measures plural types of water quality of the ballast water such as, for example, the TRO concentration. The measurement device 52 includes the housing 4, the water discharge part 7, the reagent supply part 8, the buffer solution supply part 10, the display and input part 12, and the control part 14 that are described in the first embodiment. The measurement device 52 includes a first measuring part 54-1 (hereinafter, referred to as "measuring part 54-1"), a second measuring part 54-2 (hereinafter, referred to as "measuring part 54-2"), a dilution water supply part 56, and a cleaning liquid supply part 58.

The housing 4 accommodates therein the measuring parts 54-1 and 54-2, the water discharge part 7, the reagent supply part 8, the buffer solution supply part 10, the display and input part 12, the control part 14, the dilution water supply part 56, and the cleaning liquid supply part 58, and aggregates these members in the housing. The housing 4 is, for example, a metal housing and imparts stiffness to the measurement device 52.

The measuring part 54-1 includes the measuring gauge 20-1, the water supply pipe 22-1, the water discharge pipe 24-1, and the water supply pump 26-1. The measuring gauge 20-1, the water supply pipe 22-1, the water discharge pipe 24-1, and the water supply pump 26-1 are same as those in the first embodiment and will not again be described. The measuring part 54-1 further includes a first open-close valve 60-1 (hereinafter, referred to as "open-close valve 60-1"), a first strainer 62-1 (hereinafter, referred to as "strainer 62-1"), a first pressure gauge 64-1 (hereinafter, referred to as "pressure gauge 64-1"), and a first bypassing path 66-1 (hereinafter, referred to as "bypassing path 66-1").

The open-close valve 60-1 is installed on the water supply pipe 22-1, causes the ballast water BW1 to pass therethrough in its open state, and blocks the passage of the ballast water BW1 in its closed state. The open-close valve 60-1 is, for example, an entrance valve of the measuring part 54-1, and only has to be an automatic valve that operates by an instruction of the control part 14, or a manual valve.

The strainer 62-1 is installed on the water supply pipe 22-1 and functions as a filter that filters the suspended solids in the ballast water BW1.

The pressure gauge 64-1 is installed on the water supply pipe 22-1. The pressure gauge 64-1 is arranged upstream the water supply pump 26-1 and detects the entrance pressure of the ballast water BW1.

The bypassing path 66-1 is connected to the water supply pipe 22-1 and the water discharge pipe 24-1, and forms a bypassing path for the measuring part 54-1. The bypassing path 66-1 includes a bypass valve 68-1, causes the ballast water BW1 to bypass by the open state of the bypass valve 68-1, and blocks the bypassing of the ballast water BW1 by the closed state thereof.

The measuring part 54-2 includes the measuring gauge 20-2, the water supply pipe 22-2, the water discharge pipe 24-2, and the water supply pump 26-2. The measuring gauge 20-2, the water supply pipe 22-2, the water discharge pipe 24-2, and the water supply pump 26-2 are same as those in the first embodiment and will not again be described. The measuring part 54-2 further includes a second open-close valve 60-2 (hereinafter, referred to as “open-close valve 60-2”), a second strainer 62-2 (hereinafter, referred to as “strainer 62-2”), a second pressure gauge 64-2 (hereinafter, referred to as “pressure gauge 64-2”), and a second bypassing path 66-2 (hereinafter, referred to as “bypassing path 66-2”).

The open-close valve 60-2 is installed on the water supply pipe 22-2, causes the ballast water BW2 to pass therethrough in its open state, and blocks the passage of the ballast water BW2 in its closed state. The open-close valve 60-2 is, for example, an entrance valve of the measuring part 54-2, and only has to be an automatic valve that operates by an instruction of the control part 14, or a manual valve.

The strainer 62-2 is installed on the water supply pipe 22-2 and functions as a filter that filters the suspended solids in the ballast water BW2.

The pressure gauge 64-2 is installed on the water supply pipe 22-2. The pressure gauge 64-2 is arranged upstream the water supply pump 26-2 and detects the entrance pressure of the ballast water BW2.

The bypassing path 66-2 is connected to the water supply pipe 22-2 and the water discharge pipe 24-2, and forms a bypassing path for the measuring part 54-2. The bypassing path 66-2 includes a bypass valve 68-2, causes the ballast water BW2 to bypass by the open state of the bypass valve 68-2, and blocks the bypassing of the ballast water BW2 by the closed state thereof.

The measuring part 54-1 and the measuring part 54-2 are arranged, for example, to be symmetric in the right-and-left direction about an extended line passing through the water discharge part 7. The arrangement of each of the measuring part 54-1 and the measuring part 54-2 does not need to be learned separately from each other and the load of handling the measurement device 52 is reduced by arranging the measuring part 54-1 and the measuring part 54-2 to be symmetric in the right-and-left direction.

The dilution water supply part 56 includes a dilution water pipe 70, a first dilution water pump 72-1 (hereinafter, referred to as “dilution water pump 72-1”), and a second dilution water pump 72-2 (hereinafter, referred to as “dilution water pump 72-2”). The dilution water pipe 70 is an example of the means for conveying the dilution water, and, for the dilution water pipe 70, the pipe extending from the exterior of the housing 4 is branched to form two branch pipes. One of the branch pipes is connected to the water supply pipe 22-1 of the measuring part 54-1 and the other thereof is connected to the water supply pipe 22-2 of the measuring part 54-2. The dilution water pipe 70 only has to be a pipe that avoids generation of any material variation caused by being in contact with water and is, for example, a resin pipe such as a fluorine resin pipe or a vinyl chloride pipe, a stainless steel pipe, or a metal pipe to which a corrosion prevention process is applied.

The dilution water pump 72-1 is installed on the branch pipe connected to the water supply pipe 22-1. The dilution water pump 72-1 supplies dilution water to the water supply pipe 22-1 by being driven. The dilution water pump 72-2 is installed on the branch pipe connected to the water supply pipe 22-2. The dilution water pump 72-2 supplies the dilution water to the water supply pipe 22-2 by being driven. The dilution water dilutes the types of ballast water BW1 and BW2.

The cleaning liquid supply part 58 includes a cleaning liquid container 74, a cleaning liquid pipe 76, a first cleaning liquid supply pump 78-1 (hereinafter, referred to as “cleaning liquid supply pump 78-1”), and a second cleaning liquid supply pump 78-2 (hereinafter, referred to as “cleaning liquid supply pump 78-2”). The cleaning liquid container 74 is an example of the cleaning liquid store part that stores cleaning liquid. The cleaning liquid container 74 is connected to the water supply pipes 22-1 and 22-2 through the cleaning liquid pipe 76. The cleaning liquid pipe 76 is an example of the means for conveying the cleaning liquid and, for the cleaning liquid pipe 76, the pipe connected to the cleaning liquid container 74 is branched to form two branch pipes. One of the branch pipes is connected to the water supply pipe 22-1 and the other branch pipe is connected to the water supply pipe 22-2. The cleaning liquid pipe 76 only has to be a pipe that avoids generation of any material variation caused by being in contact with water and is, for example, a resin pipe such as a fluorine resin pipe or a vinyl chloride pipe, a stainless steel pipe, or a metal pipe to which a corrosion prevention process is applied.

The cleaning liquid supply pump 78-1 is installed on the branch pipe connected to the water supply pipe 22-1. The cleaning liquid supply pump 78-1 supplies the cleaning liquid in the cleaning liquid container 74 to the water supply pipe 22-1, by being driven. The cleaning liquid supply pump 78-2 is installed on the branch pipe connected to the water supply pipe 22-2. The cleaning liquid supply pump 78-2 supplies the cleaning liquid in the cleaning liquid container 74 to the water supply pipe 22-2, by being driven.

The control part 14 has the configuration described in the first embodiment and will not again be described. In addition to executing the information processing described in the first embodiment, the processor 40 of the control part 14 executes information processing such as instruction for opening and closing of each of the valves, acquisition of pressure information acquired by each of the pressure gauges 64-1 and 64-2, and processes based on the pressure information such as, for example, measurement determination for each of the types of ballast water BW1 and BW2. The I/O 44 of the control part 14 is connected by wire or by radio to the connection instruments described in the first embodiment and, in addition, is connected by wire or by radio to connection instruments such as the valves and the pressure gauges 64-1 and 64-2. The other configuration of the control part 14 is similar to that of the control part 14 in the first embodiment and will not again be described.

In this embodiment, the dilution water supply part 56 is included and each of the types of ballast water BW1 and BW2 can therefore be diluted separately from each other by supplying the dilution water thereto. The supply amount of the dilution water only has to be adjusted by the control part 14 such that the TRO concentration of each of the types of ballast water BW1 and BW2 after the dilution is in the range for good measurement by each of the measuring gauges 20-1 and 20-2 (such as, for example, 0 to 6 mg/L in terms of chlorine). When each of the types of ballast water BW1 and BW2 is diluted, the control part 14 only has to calculate the TRO concentration of each of the types of ballast water BW1 and BW2 taking into consideration the supply amounts of the types of ballast water BW1 and BW2, and the dilution water. The measurement precision for the TRO concentration can be improved by diluting each of the types of ballast water BW1 and BW2 such that the TRO concentration is in the range for good measurement by each of the measuring gauges 20-1 and 20-2.

In this embodiment, the measuring gauges 20-1 and 20-2, and the water supply pipes 22-1 and 22-2 can be cleaned by supplying the cleaning liquid thereto because the cleaning liquid supply part 58 is connected to the water supply pipes 22-1 and 22-2. Because the measuring gauges 20-1 and 20-2, and the water supply pipes 22-1 and 22-2 are cleaned, occurrence of any abnormality in the measurement result due to any pollution of the measuring gauges 20-1 and 20-2, and the water supply pipes 22-1 and 22-2 is suppressed.

[Process Procedure for Water Quality Measurement for Types of Ballast Water BW1 and BW2]

Figure 8:
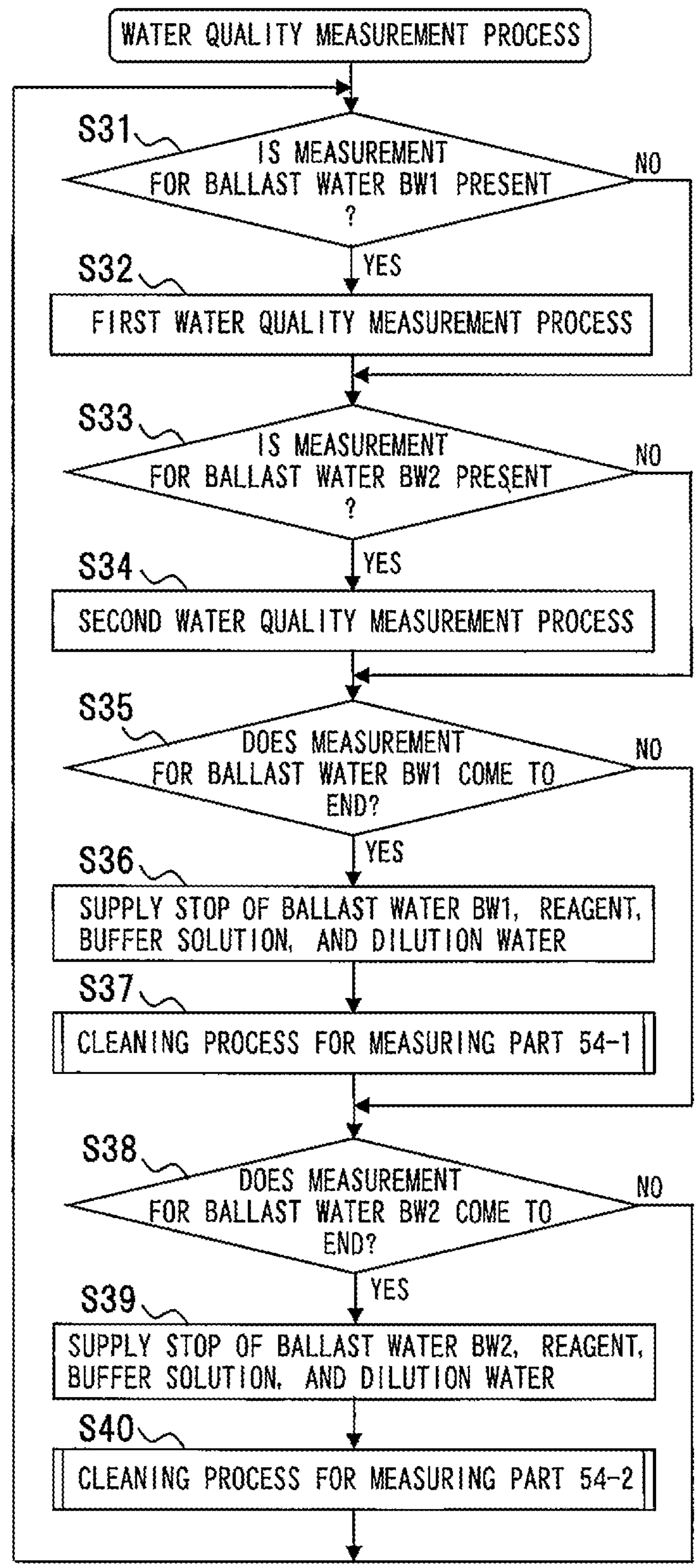
FIG. 8 is a flowchart of an example of a process procedure for water quality measurement.

The process procedure for the water quality measurement for the types of ballast water BW1 and BW2 will be described with reference to FIG. 8. FIG. 8 is a flowchart of an example of the process procedure for the water quality measurement. The process procedure for the water quality measurement is an example of the ballast water measurement method of the present invention, and is processed by the control part 14. In FIG. 8, "step S" represents a stage of the process.

The control part 14 determines whether measurement for the ballast water BW1 is present (step S31). When the control part 14 determines that the measurement for the ballast water BW1 is present (YES of step S31), the control part 14 executes a first water quality measurement process (step S32). In the first water quality measurement process, the control part 14 operates the dilution water pump 72-1 to supply the dilution water to the ballast water BW1. The other steps of the first water quality measurement process are same as those of the first water quality measurement process (steps S12 to S14) described in the first embodiment and will not again be described. When the control part 14 determines that the measurement for the ballast water BW1 is not present (NO of step S31), the control part 14 does not execute the first water quality measurement process (step S32). Whether the measurement for the ballast water BW1 is present only has to be determined based on, for example, the pressure detected by the pressure gauge 64-1, or may be determined by acquiring the ballast water process information from the ballast water process equipment. The ballast water process information only has to include, for example, information that indicates whether the ballast water process is currently executed.

The control part 14 determines whether measurement for the ballast water BW2 is present (step S33). When the control part 14 determines that the measurement for the ballast water BW2 is present (YES of step S33), the control part 14 executes a second water quality measurement process (step S34). In the second water quality measurement process, the control part 14 operates the dilution water pump 72-2 to supply the dilution water to the ballast water BW2. The other steps of the second water quality measurement process are same as those of the second water quality measurement process (steps S16 to S18) described in the first embodiment and will not again be described. When the control part 14 determines that the measurement for the ballast water BW2 is not present (NO of step S33), the control part 14 does not execute the second water quality measurement process (step S34). Whether the measurement for the ballast water BW2 is present only has to be determined based on, for example, the pressure detected by the pressure gauge 64-2, or may be determined by acquiring the ballast water process information from the ballast water process equipment.

The control part 14 determines whether the measurement for the ballast water BW1 comes to an end (step S35). When the control part 14 determines that the measurement for the ballast water BW1 comes to an end (YES of step S35), the control part 14 stops the water supply pump 26-1, the reagent supply pump 32-1, the buffer solution supply pump 38-1, and the dilution water pump 72-1 to stop the supply of the ballast water BW1, the reagent, the buffer solution, and the dilution water (step S36) and executes a cleaning process for the measuring part 54-1 (step S37). When the control part 14 determines that the measurement for the ballast water BW1 does not come to an end (NO of step S35), that is, the measurement for the ballast water BW1 is present or is currently discontinued, the control part 14 does not execute step S36 and step S37. Whether the measurement for the ballast water BW1 comes to an end only has to be determined based on, for example, the pressure detected by the pressure gauge 64-1, or may be determined by acquiring the ballast water process information from the ballast water process equipment.

The control part 14 determines whether the measurement for the ballast water BW2 comes to an end (step S38). When the control part 14 determines that the measurement for the ballast water BW2 comes to an end (YES of step S38), the control part 14 stops the water supply pump 26-2, the reagent supply pump 32-2, the buffer solution supply pump 38-2, and the dilution water pump 72-2 to stop the supply of the ballast water BW2, the reagent, the buffer solution, and the dilution water (step S39) and executes a cleaning process for the measuring part 54-2 (step S40). When the control part 14 determines that the measurement for the ballast water BW2 does not come to an end (NO of step S38), that is, the measurement for the ballast water BW2 is present or is currently discontinued, the control part 14 does not execute step S39 and step S40. Whether the measurement for the ballast water BW2 comes to an end only has to be determined based on, for example, the pressure detected by the pressure gauge 64-2, or may be determined by acquiring the ballast water process information from the ballast water process equipment.

The control part 14 repeats this process procedure to be able to continuously or intermittently measure the water quality of each of the types of ballast water BW1 and BW2. The first water quality measurement process and the second water quality measurement process are each processed separately from each other, and the control part 14 therefore not only can process both of the first water quality measurement process and the second water quality measurement process but also can process either the first water quality measurement process or the second water quality measurement process.

[Cleaning Process for Measuring Parts 54-1 and 54-2]

Figure 9:
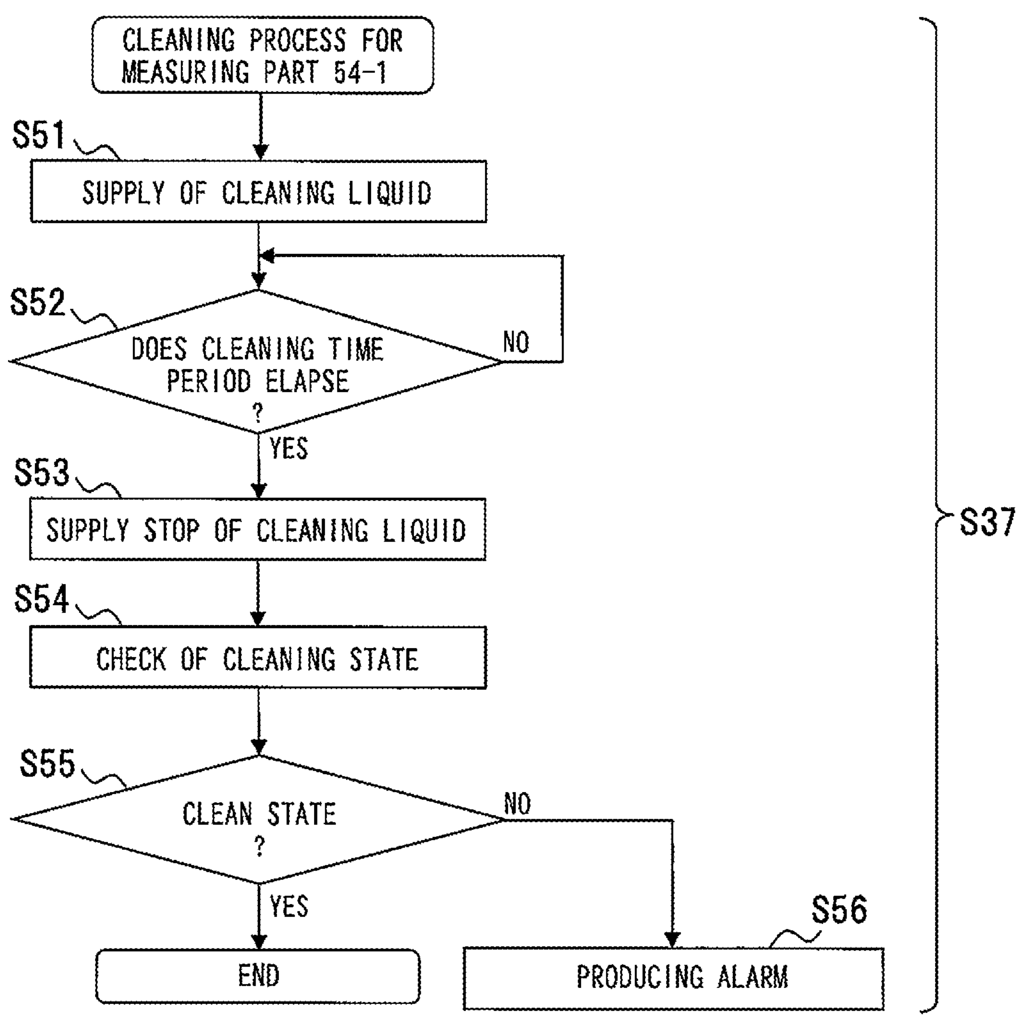
FIG. 9 is a flowchart of an example of a process procedure for a cleaning process of the measuring part.

The cleaning process for the measuring part 54-1 (step S37) will be described with reference to FIG. 9. FIG. 9 depicts an example of the process procedure for the cleaning process for the measuring part. The process procedure for the cleaning process for the measuring part is a process as a subroutine of the cleaning process for the measuring part 54-1 (step S37). In FIG. 9, "step S" represents a stage of the process.

In the cleaning process for the measuring part 54-1, the control part 14 operates the cleaning liquid supply pump 78-1 to supply the cleaning liquid in the cleaning liquid container 74 to the water supply pipe 22-1 (step S51). The cleaning liquid supplied to the water supply pipe 22-1 passes through the water supply pipe 22-1 and the measuring gauge 20-1 to clean these, and is discharged to the exterior of the measurement device 52 through the water discharge pipe 24-1 and the water discharge part 7.

The control part 14 determines whether a cleaning time period set in advance elapses after the start of the supply of the cleaning liquid (step S52). When the control part 14 determines that the cleaning time period does not yet elapse (NO of step S52), the control part 14 repeats step S52 until the cleaning time period elapses. The cleaning time period only has to be, for example, a time period necessary for the cleaning of the water supply pipe 22-1 and the measuring gauge 20-1. The set cleaning time period is set in, for example, the memory part 42 of the control part 14. When the control part 14 determines that the cleaning time period elapses (YES of step S52), the control part 14 stops the supply of the cleaning liquid (step S53) and checks the cleaning state of the measuring gauge 20-1 of the measuring part 54-1 (step S54). For the check of the cleaning state, for example, the control part 14 only has to acquire the measured value from the measuring gauge 20-1 after the cleaning and determine whether this measured value is a normal value. When the control part 14 determines that the measuring gauge 20-1 is in a clean state (YES of step S55), the control part 14 causes the cleaning process to come to an end. When the control part 14 determines that the measuring gauge 20-1 is not in the clean state (NO of step S55), that is, when the cleaning is insufficient, the control part 14 produces an alarm (S56) and discontinues the cleaning process.

The cleaning process for the measuring part 54-2 (step S40) only has to be processed in the same manner as that of the cleaning process for the measuring part 54-1 (step S37) and will not again be described.

Effects of Second Embodiment (1) The effects described in the first embodiment can be achieved.

(2) The types of ballast water BW1 and BW2 can each be diluted such that, for example, the TRO concentration of each of the types of ballast water BW1 and BW2 is in the range for good measurement by each of the measuring gauges 20-1 and 20-2, and the measurement precision for the TRO concentration can be improved because the measurement device 52 includes the dilution water supply part 56. The area necessary for installing the dilution water supply part 56 can be reduced because the supply of the dilution water is used in common by the two measuring parts 54-1 and 54-2. The installation area for the measurement device 52 can therefore be reduced and the work area necessary for the operation or the maintenance of the measurement device 52 can be reduced.

(3) The clean state of each of the measuring gauges 20-1 and 20-2 is maintained and occurrence of any abnormality due to any pollution of each of the measuring gauges 20-1 and 20-2 is suppressed because the measurement device 52 includes the cleaning liquid supply part 58. The fact is prevented that any measurement abnormality due to any pollution of each of the measuring gauges 20-1 and 20-2 is left untreated and the measurement is repeated in the abnormal state for the measurement, because the clean state of each of the measuring gauges 20-1 and 20-2 can be monitored. The area necessary for installing the cleaning liquid supply part 58 is reduced because the supply of the cleaning liquid is used in common by the two measuring parts 54-1 and 54-2. The installation area for the measurement device 52 can therefore be reduced and the work area necessary for the operation or the maintenance of the measurement device 52 can be reduced.

(4) In the cleaning process for each of the measuring parts 54-1 and 54-2 in the above embodiment, when the measuring gauges 20-1 and 20-2 of the measuring parts 54-1 and 54-2 are each not in the clean state, that is, when the cleaning is insufficient, an alarm is produced and the abnormality is thereby notified of. Any water quality measurement using each of the measuring gauges 20-1 and 20-2 each in the insufficient cleaning state can be prevented and any measurement under the abnormal state can be prevented from being continued, by this notification of the abnormality. Because any measurement under the abnormal state is prevented, proper injection of the reagent can be maintained and high precision for the water quality measurement can be maintained, and any increase of the cost for the reagent due to excessive injection of the reagent can be prevented.

Modification Examples (1) The modification examples described in the first embodiment are applicable to the second embodiment.

(2) The measurement device 52 includes the dilution water supply part 56 and the cleaning liquid supply part 58 in the above embodiment while these components may selectively be included therein. The measuring part 54-1 of the measurement device 52 includes the open-close valve 60-1, the strainer 62-1, the pressure gauge 64-1, and the bypassing path 66-1 while these components may selectively be included therein. The measuring part 54-2 of the measurement device 52 includes the open-close valve 60-2, the strainer 62-2, the pressure gauge 64-2, and the bypassing path 66-2 while these components may selectively be included therein. These modification examples can also achieve the effects described in the first embodiment.

(3) The above embodiment includes the cleaning process for each of the measuring parts 54-1 and 54-2, and the measuring parts 54-1 and 54-2 are cleaned when the measurement for each of the types of ballast water BW1 and BW2 is ended while the operation may be switched during the measurement for each of the types of ballast water BW1 and BW2 such that the measuring parts 54-1 and 54-2 are cleaned, or the measuring parts 54-1 and 54-2 may be cleaned during discontinuation of the measurement for each of the types of ballast water BW1 and BW2. Otherwise, the cleaning may be started associated with detection of any abnormal value of the TRO concentration as the trigger therefor, the cleaning may be started associated with censoring of any pollution or any insufficient cleaning of a measurement cell included in each of the measuring gauges 20-1 and 20-2, or the cleaning may be started based on a time period elapsing from the previous cleaning process.

Third Embodiment

Figure 10:
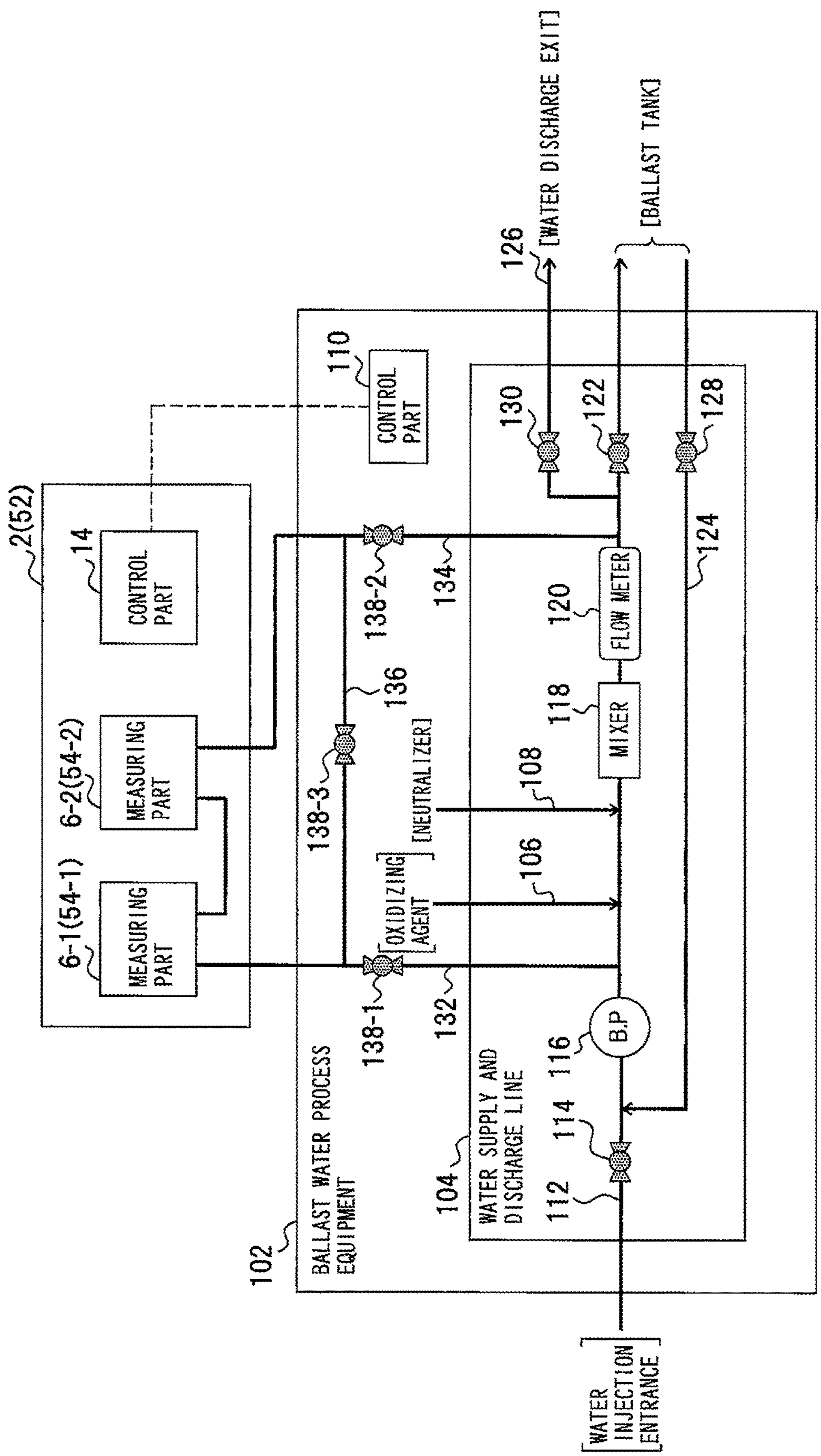
FIG. 10 is a diagram of an example of connection of the ballast water measurement device and ballast water process equipment.

A third embodiment will be described with reference to FIG. 10. FIG. 10 depicts an example of connection between the ballast water measurement device and the ballast water process equipment. In FIG. 10, parts same as those in FIG. 1 or FIG. 7 are given the same reference numerals. In this embodiment, the measurement device 2 described in the first embodiment may be connected to ballast water process equipment 102, or the measurement device 52 described in the second embodiment may be connected to the ballast water process equipment 102. The measurement device 2 or 52 and the ballast water process equipment 102 depicted in FIG. 10 are each an example and the present invention is not limited to this configuration.

[Ballast Water Process Equipment 102]

The ballast water process equipment 102 includes a water supply and discharge line 104, an oxidizing agent supply line 106, a neutralizer supply line 108, and a control part 110.

The water supply and discharge line 104 includes a main line 112, and the main line 112 includes a ballast water injection valve 114, a ballast pump 116, a mixer 118, a flow meter 120, and a ballast tank entrance valve 122. The main line 112 connects the injection entrance for the ballast water and the ballast tank to each other. The ballast water injection valve 114 is installed downstream the water injection entrance, and causes the ballast water supplied from the water injection entrance to pass therethrough or blocks the ballast water by opening or closing of the valve. The ballast pump 116 is installed on the downstream side of the ballast water injection valve 114, and causes the ballast water to flow into the mixer 118 by being driven. The mixer 118 is installed downstream the ballast pump 116, and mixes the oxidizing agent or the neutralizer injected between the ballast pump 116 and the mixer 118, into the ballast water. The flow meter 120 is installed downstream the mixer 118 and measures the flow amount of the ballast water that includes the oxidizing agent or the neutralizer. The ballast tank entrance valve 122 is installed downstream the flow meter 120, and causes the ballast water to pass therethrough or blocks the passage of the ballast water by opening or closing of the valve. The ballast water passing through the ballast tank entrance valve 122 is poured into the ballast tank.

The water supply and discharge line 104 further includes a branch line 124 that is disposed in parallel to the main line 112, and a water discharge line 126. The branch line 124 includes a ballast tank exit valve 128. The water discharge line 126 includes a ballast water discharge valve 130. The branch line 124 connects the main line 112 between the ballast water injection valve 114 and the ballast pump 116, and the ballast tank with each other. The water discharge line 126 connects the main line 112 between the flow meter 120 and the ballast tank entrance valve 122, and the water discharge exit with each other. The ballast tank exit valve 128 causes the ballast water in the branch line 124 to pass therethrough or blocks the passage of the ballast water by opening or closing of the valve. The ballast water discharge valve 130 causes the ballast water in the water discharge line 126 to pass therethrough or blocks the passage of the ballast water by opening or closing of the valve.

When the ballast water injection valve 114 and the ballast tank entrance valve 122 are opened, and the ballast tank exit valve 128 and the ballast water discharge valve 130 are closed, a water supply path for the ballast water is formed. When the ballast pump 116 is operated, the ballast water passes through the main line 112 and is supplied to the ballast tank.

When the ballast water injection valve 114 and the ballast tank entrance valve 122 are closed, and the ballast tank exit valve 128 and the ballast water discharge valve 130 are opened, a water discharge path for the ballast water is formed. When the ballast pump 116 is operated, the ballast water in the ballast tank flows through the branch line 124, the ballast pump 116, the mixer 118, and the flow meter 120 in this order and passes through the water discharge line 126 to be discharged from the water discharge exit to the sea.

The oxidizing agent supply line 106 supplies the oxidizing agent to the main line 112 on the upstream side of the mixer 118.

The neutralizer supply line 108 supplies the neutralizer to the main line 112 on the upstream side of the mixer 118. The neutralizer is, for example, sodium sulfite, sodium bisulfite (sodium hydrogen sulfite), or sodium thiosulfate.

The control part 110 is connected to the valves, the ballast pump 116, the flow meter 120, and the control part 14 of the measurement device 2 (or the measurement device 52), and controls opening or closing of each of the valves, operation or stoppage of the ballast pump 116, and the supply amounts of the oxidizing agent and the neutralizer. The control part 110 receives the measured value of the flow meter 120 and the water quality information on the ballast water, and determines or records the process state of the ballast water.

[Connection between Measurement Device 2 and Ballast Water Process Equipment 102]

The measuring part 6-1 of the measurement device 2 is connected by a connection pipe 132 to the main line 112 on the upstream side of the oxidizing agent supply line 106 and the neutralizer supply line 108. With the above connection, the measuring part 6-1 receives the supply of the ballast water BW1 before the supply of the oxidizing agent or the neutralizer thereto and measures the water quality of the ballast water BW1.

The measuring part 6-2 of the measurement device 2 is connected by a connection pipe 134 to the main line 112 on the downstream side of the mixer 118. With this connection, the measuring part 6-2 receives the supply of the ballast water BW2 after the supply of the oxidizing agent or the neutralizer thereto and measures the water quality of the ballast water BW2. For the measuring part 6-1 and the measuring part 6-2 of the measurement device 2, the connection pipes 132 and 134 to the main line 112 communicate with each other by a connection pipe 136, and can be switched by a switching mechanism such as, for example, switching valves 138-1, 138-2, and 138-3 such that only either one measuring part thereof measures the ballast water. The connection pipe 136 and the switching mechanism can switch the connection between the measuring parts 6-1 and 6-2, and the main line 112. This connection switching enables the ballast water BW2 after the supply of the oxidizing agent or the neutralizer thereto to be supplied to the measuring part 6-1 and the measuring part 6-1 to measure the water quality of the ballast water BW2. The connection switching enables the ballast water BW1 before the supply of the oxidizing agent or the neutralizer thereto to be supplied to the measuring part 6-2 and the measuring part 6-2 to measure the water quality of the ballast water BW1.

[Process Sequence for Measurement Device 2 and Ballast Water Process Equipment 102]

Figure 11:
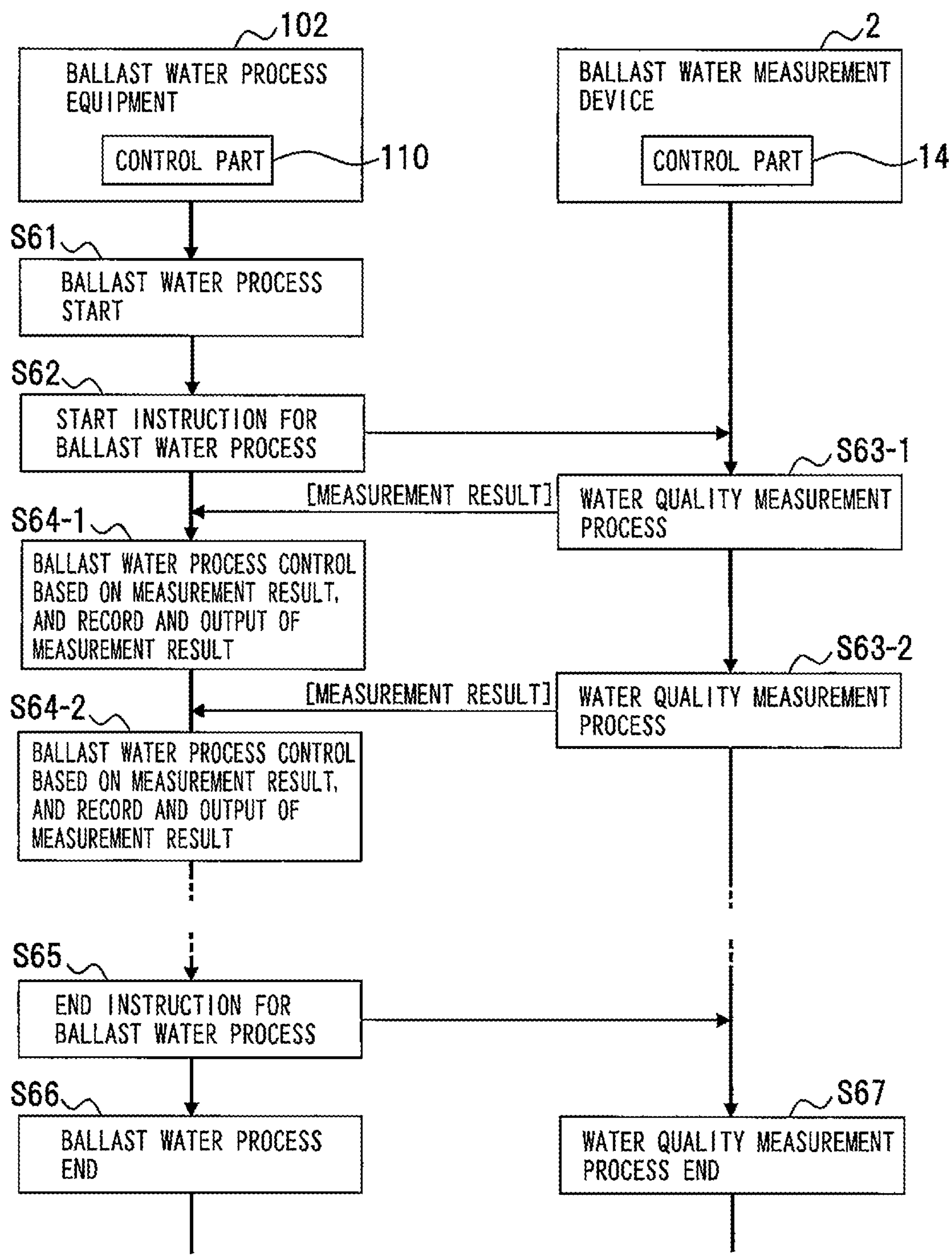
FIG. 11 is a diagram of an example of a process sequence for the ballast water measurement device and the ballast water process equipment.

FIG. 11 depicts an example of the process sequence for the ballast water measurement device and the ballast water process equipment. In FIG. 11, "step S" represents a stage of the process.

When the control part 110 of the ballast water process equipment 102 starts the ballast water process, that is, the supply of the ballast water or the discharge of the ballast water (step S61), the control part 110 instructs a start instruction for the ballast water process to the control part 14 of the measurement device 2 (step S62). The control part 14 receives the start instruction for the ballast water process, executes the first and the second water quality measurement processes, and notifies the control part 110 of the measurement result that includes the water quality information on each of the types of ballast water BW1 and BW2 (step S63-1). The control part 110 controls the ballast water process based on the measurement result, records the measurement result, and outputs the measurement result to the ship (step S64-1). Step S63-1 and step S64-1 are repeated until the ballast water process comes to an end (step S63-2, step S64-2, and so on). The control part 110 instructs an end instruction for the ballast water process to the control part 14 (step S65) and ends the ballast water process (step S66). The control part 14 receives the end instruction for the ballast water process and ends the water quality measurement process (step S67).

[Connection between Measurement Device 52 and Ballast Water Process Equipment 102, and Process Sequence for Measurement Device 52 and Ballast Water Process Equipment 102]

The measurement device 52 and the ballast water process equipment 102 can be connected to each other in the same manner as that for the measurement device 2 and the ballast water process equipment 102. The process sequence for the measurement device 2 and the ballast water process equipment 102 is applicable to the measurement device 52 and the ballast water process equipment 102. When the water quality measurement is started or ended using the pressure detected by each of the pressure gauges 64-1 and 64-2 of the measurement device 52, step S62 and step S65 of the above process sequence only have to be not executed. The process load on the control part 110 can be reduced. When either the measuring part 6-1 or the measuring part 6-2 of the measurement device 2 is out of order, the connection between the measuring parts 6-1 and 6-2, and the main line 112 is switched by the switching mechanism and the ballast water is measured by only either one measuring part. Discharge of, for example, any ballast water having the neutralizer insufficiently injected therein can thereby be avoided.

Effects of Third Embodiment (1) The water quality of the ballast water before and that after the ballast water process by the ballast water process equipment 102 installed in the ship can be measured by the one measurement device 2 or the one measurement device 52. The installation area for the measurement device 2 or the measurement device 52 can therefore be reduced, and the work area necessary for the operation or the maintenance of the measurement device 2 or the measurement device 52 can be reduced. When the ballast water process equipment 102 is linked to the one measurement device 2 or the one measurement device 52, the ballast water process equipment 102 can execute the ballast water process and the water quality management of the ballast water, and the linkage between the ballast water process equipment 102 and the measurement device 2 or 52 is easy. The equipment management load of the measurement device 2 or 52, and the remaining amount management load of the reagent and the buffer solution are reduced. As to the water quality measurement of the ballast water, the shipmen do not need to maintain or manage any plural measurement devices, and the equipment management load on the shipmen is reduced.

Modification Examples (1) The water quality of the ballast water may be measured using the ballast water before and that after the ballast water process, and may be measured using the ballast water either before or after the ballast water process. For the water quality measurement of the ballast water before the ballast water process, the ballast water process can be controlled using feedforward of the measurement result. For the water quality measurement of the ballast water after the ballast water process, the ballast water process can be controlled using feedback of the measurement result, and the water quality of the ballast water after the ballast water process can actually be measured.

(2) When the device specification is caused to differ between the measuring parts 6-1 and 6-2 or the measuring parts 54-1 and 54-2, it is preferred that the setting be made such that, for example, the measuring part 6-1 or the measuring part 54-1 has a wider measurement range than the other one and the measuring part 6-2 or the measuring part 54-2 has a higher sensitivity than the other one. With this setting, the ballast water before the neutralization process including a large amount of oxidizing agent can be measured in a wide range using the measuring part 6-1 or the measuring part 54-1 having the wider measurement range, and the ballast water after the neutralization process including a small amount of or no oxidizing agent can be highly precisely measured using the measuring part 6-2 or the measuring part 54-2 having the higher sensitivity. When the ballast water is taken in the ship, the connection is switched by the switching mechanism and the ballast water after the injection of the oxidizing agent can be measured using the measuring part 6-1 or the measuring part 54-1.

As above, the most preferred embodiment etc. of the present invention have been described. The present invention is not limited to the above description. Those skilled in the art can make various modifications and changes thereto based on the gist of the invention described in the claims or disclosed in the description. Not to mention, such modifications and changes are encompassed in the scope of the present invention.

INDUSTRIAL APPLICABILITY

The present invention enables measurement of the water quality of ballast water such as, for example, the TRO concentration, in a ballast water process of annihilating any organisms in the ballast water by adding an oxidizing agent such as sodium hypochlorite or ozone to the ballast water. For a ship executing the ballast water process therein, the present invention is useful for water quality measurement for the ballast water and, in addition, is useful for the water quality measurement for other types of water to which a drug or drugs such as, for example, an oxidizing agent and a neutralizer therefor are added.

EXPLANATIONS OF LETTERS OR NUMBERS

2, 52 measurement device
4 housing
6-1, 6-2, 54-1, 54-2 measuring part
7 water discharge part
8 reagent supply part
10 buffer solution supply part
12 display and input part
14 control part
20-1, 20-2 measuring gauge
22-1, 22-2 water supply pipe
24-1, 24-2 water discharge pipe
26-1, 26-2 water supply pump
28 reagent container
30 reagent pipe
32-1, 32-2 reagent supply pump
34 buffer solution container
36 buffer solution pipe
38-1, 38-2 buffer solution supply pump
40 processor
42 memory part
44 I/O
50-1, 50-2 backflow preventing part
56 dilution water supply part
58 cleaning liquid supply part
60-1, 60-2 open-close valve
62-1, 62-2 strainer
64-1, 64-2 pressure gauge
66-1, 66-2 bypassing path

68-1, 68-2 bypass valve
70 dilution water pipe
72-1, 72-2 dilution water pump
74 cleaning liquid container
76 cleaning liquid pipe
78-1, 78-2 cleaning liquid supply pump

The invention claimed is:

1. A ballast water measurement device comprising:

a first measuring part that measures water quality of a first ballast water, with referring to ballast water before processing as the first ballast water and ballast water after the processing as a second ballast water;

a second measuring part that measures water quality of the second ballast water;

a reagent supply part that is connected to the first measuring part and the second measuring part, and that supplies a reagent from one reagent container to the first measuring part and the second measuring part;

a water discharge part that is connected to the first measuring part and the second measuring part, and that discharges the first ballast water and the second ballast water each after the measurement; and a housing that accommodates therein the first measuring part, the second measuring part, the reagent supply part, and the water discharge part.

2. The ballast water measurement device according to claim 1, further comprising a buffer solution supply part that is connected to the first measuring part and the second measuring part, and that supplies a buffer solution from one buffer solution container to the first measuring part and the second measuring part.

3. The ballast water measurement device according to claim 1, further comprising a cleaning liquid supply part that is connected to the first measuring part and the second measuring part, and that supplies a cleaning liquid from one cleaning liquid container to the first measuring part and the second measuring part.

4. The ballast water measurement device according to claim 1, wherein the ballast water measurement device is installed in a ship and measures the water quality of the ballast water before and that after the ballast water process by ballast water process equipment installed in the ship.

5. The ballast water measurement device according to claim 1, wherein the reagent in the reagent container is colored.

6. A ballast water measurement method comprising:

supplying a first ballast water to a first measuring part in a housing, with referring to ballast water before processing as the first ballast water and ballast water after the processing as a second ballast water;

supplying the second ballast water to a second measuring part in the housing;

supplying a reagent from one reagent container in the housing to the first measuring part and the second measuring part;

measuring the first ballast water comprising the reagent using the first measuring part;

measuring the second ballast water comprising the reagent using the second measuring part; and discharging the first ballast water and the second ballast water each after the measurement from one water discharge part in the housing.

* * * * *